(12) United States Patent
Bakos et al.

(10) Patent No.: US 8,262,563 B2
(45) Date of Patent: Sep. 11, 2012

(54) ENDOSCOPIC TRANSLUMENAL ARTICULATABLE STEERABLE OVERTUBE

(75) Inventors: Gregory J. Bakos, Mason, OH (US); James T. Spivey, Cincinnati, OH (US); William D. Fox, New Richmond, OH (US); Bernard C. McDermott, Kiltimagh (IE); Micheal E. Kelly, Tubber (IE); Michelle M. Guinan, Merlin Park (IE)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1093 days.

(21) Appl. No.: 12/172,782

(22) Filed: Jul. 14, 2008

(65) Prior Publication Data

US 2010/0010299 A1  Jan. 14, 2010

(51) Int. Cl.
*A61B 1/00* (2006.01)
*A61M 25/00* (2006.01)

(52) U.S. Cl. ........ 600/141; 600/114; 600/115; 600/139; 600/140; 600/142; 600/146; 604/524; 604/525; 604/526

(58) Field of Classification Search .................. 600/106, 600/108, 114, 115, 138, 139, 140, 141, 145, 600/150, 142, 144; 604/524, 525, 526, 527, 604/534
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A * | 5/1960 | De Graaf ........................ 73/242 |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |

(Continued)

FOREIGN PATENT DOCUMENTS

AU  666310 B2  2/1996

(Continued)

OTHER PUBLICATIONS

International Search Report for PCT/US2009/050451, Dec. 11, 2009 (10 pages).

(Continued)

*Primary Examiner* — Cris L. Rodriguez
*Assistant Examiner* — Rynae Boler

(57) ABSTRACT

An apparatus having an elongate hollow metal body extending along a longitudinal axis is disclosed. The hollow body defines a central opening and has a predetermined wall thickness. A pattern of laser cut slits is formed into the body. The slits define a plurality of articulatable elements. The plurality of articulatable elements enable active articulation of the body in a first plane and passive deflection in planes orthogonal to the first plane.

29 Claims, 20 Drawing Sheets

U.S. PATENT DOCUMENTS

| | | |
|---|---|---|
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A * | 12/1990 | Gouda ......................... 600/144 |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |

| Patent | Date | Inventor |
|---|---|---|
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,456,667 A * | 10/1995 | Ham et al. .................... 604/107 |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |

| | | | | | | |
|---|---|---|---|---|---|---|
| 5,911,737 A | 6/1999 | Lee et al. | | 6,206,877 B1 | 3/2001 | Kese et al. |
| 5,916,147 A | 6/1999 | Boury | | 6,214,007 B1 | 4/2001 | Anderson |
| 5,921,993 A | 7/1999 | Yoon | | 6,228,096 B1 | 5/2001 | Marchand |
| 5,921,997 A | 7/1999 | Fogelberg et al. | | 6,234,958 B1 | 5/2001 | Snoke et al. |
| 5,922,008 A | 7/1999 | Gimpelson | | 6,245,079 B1 | 6/2001 | Nobles et al. |
| 5,925,052 A | 7/1999 | Simmons | | 6,246,914 B1 * | 6/2001 | de la Rama et al. .......... 607/122 |
| 5,928,255 A | 7/1999 | Meade et al. | | 6,258,064 B1 | 7/2001 | Smith et al. |
| 5,928,266 A | 7/1999 | Kontos | | 6,261,242 B1 | 7/2001 | Roberts et al. |
| 5,936,536 A | 8/1999 | Morris | | 6,264,664 B1 | 7/2001 | Avellanet |
| 5,944,718 A | 8/1999 | Austin et al. | | 6,270,497 B1 | 8/2001 | Sekino et al. |
| 5,951,549 A | 9/1999 | Richardson et al. | | 6,270,505 B1 | 8/2001 | Yoshida et al. |
| 5,954,720 A | 9/1999 | Wilson et al. | | 6,277,136 B1 | 8/2001 | Bonutti |
| 5,954,731 A | 9/1999 | Yoon | | 6,283,963 B1 | 9/2001 | Regula |
| 5,957,943 A | 9/1999 | Vaitekunas | | 6,293,909 B1 | 9/2001 | Chu et al. |
| 5,957,953 A | 9/1999 | DiPoto et al. | | 6,293,952 B1 | 9/2001 | Brosens et al. |
| 5,971,995 A | 10/1999 | Rousseau | | 6,296,630 B1 | 10/2001 | Altman et al. |
| 5,972,002 A | 10/1999 | Bark et al. | | 6,322,578 B1 | 11/2001 | Houle et al. |
| 5,976,074 A | 11/1999 | Moriyama | | 6,326,177 B1 | 12/2001 | Schoenbach et al. |
| 5,976,075 A | 11/1999 | Beane et al. | | 6,328,730 B1 | 12/2001 | Harkrider, Jr. |
| 5,976,130 A | 11/1999 | McBrayer et al. | | 6,350,267 B1 | 2/2002 | Stefanchik |
| 5,976,131 A | 11/1999 | Guglielmi et al. | | 6,350,278 B1 | 2/2002 | Lenker et al. |
| 5,980,539 A | 11/1999 | Kontos | | 6,352,503 B1 | 3/2002 | Matsui et al. |
| 5,980,556 A | 11/1999 | Giordano et al. | | 6,352,543 B1 | 3/2002 | Cole |
| 5,984,938 A | 11/1999 | Yoon | | 6,355,035 B1 | 3/2002 | Manushakian |
| 5,984,939 A | 11/1999 | Yoon | | 6,361,534 B1 | 3/2002 | Chen et al. |
| 5,989,182 A | 11/1999 | Hori et al. | | 6,371,956 B1 | 4/2002 | Wilson et al. |
| 5,993,447 A | 11/1999 | Blewett et al. | | 6,379,366 B1 | 4/2002 | Fleischman et al. |
| 5,997,555 A | 12/1999 | Kontos | | 6,383,195 B1 | 5/2002 | Richard |
| 6,001,120 A | 12/1999 | Levin | | 6,383,197 B1 | 5/2002 | Conlon et al. |
| 6,004,269 A | 12/1999 | Crowley et al. | | 6,391,029 B1 | 5/2002 | Hooven et al. |
| 6,004,330 A | 12/1999 | Middleman et al. | | 6,402,735 B1 * | 6/2002 | Langevin ...................... 604/523 |
| 6,007,566 A | 12/1999 | Wenstrom, Jr. | | 6,406,440 B1 | 6/2002 | Stefanchik |
| 6,010,515 A | 1/2000 | Swain et al. | | 6,409,727 B1 | 6/2002 | Bales et al. |
| 6,012,494 A * | 1/2000 | Balazs ......................... 138/119 | | 6,409,733 B1 | 6/2002 | Conlon et al. |
| 6,017,356 A | 1/2000 | Frederick et al. | | 6,427,089 B1 | 7/2002 | Knowlton |
| 6,019,770 A | 2/2000 | Christoudias | | 6,431,500 B1 | 8/2002 | Jacobs et al. |
| 6,024,708 A | 2/2000 | Bales et al. | | 6,443,970 B1 | 9/2002 | Schulze et al. |
| 6,024,747 A | 2/2000 | Kontos | | 6,443,988 B2 | 9/2002 | Felt et al. |
| 6,027,522 A | 2/2000 | Palmer | | 6,447,511 B1 | 9/2002 | Slater |
| 6,030,365 A | 2/2000 | Laufer | | 6,447,523 B1 | 9/2002 | Middleman et al. |
| 6,030,634 A | 2/2000 | Wu et al. | | 6,454,783 B1 | 9/2002 | Piskun |
| 6,033,399 A | 3/2000 | Gines | | 6,454,785 B2 | 9/2002 | De Hoyos Garza |
| 6,036,685 A | 3/2000 | Mueller | | 6,458,076 B1 | 10/2002 | Pruitt |
| 6,053,927 A | 4/2000 | Hamas | | 6,464,701 B1 | 10/2002 | Hooven et al. |
| 6,066,160 A | 5/2000 | Colvin et al. | | 6,464,702 B2 | 10/2002 | Schulze et al. |
| 6,068,603 A | 5/2000 | Suzuki | | 6,475,104 B1 | 11/2002 | Lutz et al. |
| 6,068,629 A | 5/2000 | Haissaguerre et al. | | 6,485,411 B1 * | 11/2002 | Konstorum et al. .......... 600/139 |
| 6,071,233 A | 6/2000 | Ishikawa et al. | | 6,489,745 B1 | 12/2002 | Koreis |
| 6,074,408 A | 6/2000 | Freeman | | 6,491,626 B1 * | 12/2002 | Stone et al. .................. 600/141 |
| 6,086,530 A | 7/2000 | Mack | | 6,491,627 B1 | 12/2002 | Komi |
| 6,090,108 A | 7/2000 | McBrayer et al. | | 6,491,691 B1 | 12/2002 | Morley et al. |
| 6,096,046 A | 8/2000 | Weiss | | 6,493,590 B1 * | 12/2002 | Wessman et al. ............. 607/116 |
| 6,102,926 A | 8/2000 | Tartaglia et al. | | 6,494,893 B2 | 12/2002 | Dubrul et al. |
| 6,106,473 A | 8/2000 | Violante et al. | | 6,500,176 B1 | 12/2002 | Truckai et al. |
| 6,109,852 A | 8/2000 | Shahinpoor et al. | | 6,503,192 B1 | 1/2003 | Ouchi |
| 6,110,154 A | 8/2000 | Shimomura et al. | | 6,506,190 B1 | 1/2003 | Walshe |
| 6,110,183 A | 8/2000 | Cope | | 6,508,827 B1 | 1/2003 | Manhes |
| 6,113,593 A | 9/2000 | Tu et al. | | 6,514,239 B2 | 2/2003 | Shimmura et al. |
| 6,117,144 A | 9/2000 | Nobles et al. | | 6,520,954 B2 | 2/2003 | Ouchi |
| 6,117,158 A | 9/2000 | Measamer et al. | | 6,543,456 B1 | 4/2003 | Freeman |
| 6,139,555 A | 10/2000 | Hart et al. | | 6,551,270 B1 | 4/2003 | Bimbo et al. |
| 6,146,391 A | 11/2000 | Cigaina | | 6,554,829 B2 | 4/2003 | Schulze et al. |
| 6,148,222 A | 11/2000 | Ramsey, III | | 6,558,384 B2 | 5/2003 | Mayenberger |
| 6,149,653 A | 11/2000 | Deslauriers | | 6,562,035 B1 | 5/2003 | Levin |
| 6,149,662 A | 11/2000 | Pugliesi et al. | | 6,562,052 B2 | 5/2003 | Nobles et al. |
| 6,156,006 A | 12/2000 | Brosens et al. | | 6,569,159 B1 | 5/2003 | Edwards et al. |
| 6,159,200 A | 12/2000 | Verdura et al. | | 6,572,629 B2 | 6/2003 | Kalloo et al. |
| 6,165,184 A | 12/2000 | Verdura et al. | | 6,572,635 B1 | 6/2003 | Bonutti |
| 6,168,570 B1 | 1/2001 | Ferrera | | 6,575,988 B2 | 6/2003 | Rousseau |
| 6,168,605 B1 | 1/2001 | Measamer et al. | | 6,579,311 B1 | 6/2003 | Makower |
| 6,170,130 B1 | 1/2001 | Hamilton et al. | | 6,585,642 B2 | 7/2003 | Christopher |
| 6,179,776 B1 | 1/2001 | Adams et al. | | 6,585,717 B1 * | 7/2003 | Wittenberger et al. ....... 604/523 |
| 6,179,837 B1 | 1/2001 | Hooven | | 6,587,750 B2 | 7/2003 | Gerbi et al. |
| 6,183,420 B1 | 2/2001 | Douk et al. | | 6,592,559 B1 | 7/2003 | Pakter et al. |
| 6,190,353 B1 | 2/2001 | Makower et al. | | 6,592,603 B2 | 7/2003 | Lasner |
| 6,190,384 B1 | 2/2001 | Ouchi | | 6,602,262 B2 | 8/2003 | Griego et al. |
| 6,190,399 B1 | 2/2001 | Palmer et al. | | 6,605,105 B1 | 8/2003 | Cuschieri et al. |
| 6,203,533 B1 | 3/2001 | Ouchi | | 6,610,072 B1 | 8/2003 | Christy et al. |
| 6,206,872 B1 | 3/2001 | Lafond et al. | | 6,610,074 B2 | 8/2003 | Santilli |

| | | |
|---|---|---|
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 * | 8/2004 | Grabover et al. ............. 600/146 |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 * | 10/2006 | Park et al. ..................... 600/143 |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,152,488 B2 | 12/2006 | Hedrich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,232,414 B2 | 6/2007 | Gonzalez |
| 7,232,445 B2 | 6/2007 | Kortenbach et al. |

| | | | | | |
|---|---|---|---|---|---|
| 7,241,290 B2 | 7/2007 | Doyle et al. | 7,892,220 B2 | 2/2011 | Faller et al. |
| 7,244,228 B2 | 7/2007 | Lubowski | 7,896,887 B2 | 3/2011 | Rimbaugh et al. |
| 7,252,660 B2 | 8/2007 | Kunz | 7,909,809 B2 | 3/2011 | Scopton et al. |
| 7,255,675 B2 | 8/2007 | Gertner et al. | 7,914,513 B2 | 3/2011 | Voorhees, Jr. |
| 7,270,663 B2 | 9/2007 | Nakao | 7,918,869 B2 | 4/2011 | Saadat et al. |
| 7,294,139 B1 | 11/2007 | Gengler | 7,931,624 B2 | 4/2011 | Smith et al. |
| 7,301,250 B2 | 11/2007 | Cassel | 7,945,332 B2 | 5/2011 | Schechter |
| 7,306,597 B2 | 12/2007 | Manzo | 7,947,000 B2 | 5/2011 | Vargas et al. |
| 7,308,828 B2 | 12/2007 | Hashimoto | 7,963,975 B2 | 6/2011 | Criscuolo |
| 7,318,802 B2 | 1/2008 | Suzuki et al. | 7,988,685 B2 | 8/2011 | Ziaie et al. |
| 7,320,695 B2 | 1/2008 | Carroll | 8,075,587 B2 | 12/2011 | Ginn |
| 7,322,934 B2 | 1/2008 | Miyake et al. | 8,088,062 B2 | 1/2012 | Zwolinski |
| 7,323,006 B2 | 1/2008 | Andreas et al. | 2001/0049497 A1 | 12/2001 | Kalloo et al. |
| 7,329,256 B2 | 2/2008 | Johnson et al. | 2002/0022771 A1 | 2/2002 | Diokno et al. |
| 7,329,257 B2 | 2/2008 | Kanehira et al. | 2002/0022857 A1 | 2/2002 | Goldsteen et al. |
| 7,329,383 B2 | 2/2008 | Stinson | 2002/0023353 A1 | 2/2002 | Ting-Kung |
| 7,344,536 B1 | 3/2008 | Lunsford et al. | 2002/0029055 A1 | 3/2002 | Bonutti |
| 7,364,582 B2 | 4/2008 | Lee | 2002/0042562 A1 | 4/2002 | Meron et al. |
| 7,371,215 B2 | 5/2008 | Colliou et al. | 2002/0049439 A1 | 4/2002 | Mulier et al. |
| 7,381,216 B2 | 6/2008 | Buzzard et al. | 2002/0068945 A1 | 6/2002 | Sixto, Jr. et al. |
| 7,393,322 B2 | 7/2008 | Wenchell | 2002/0078967 A1 | 6/2002 | Sixto, Jr. et al. |
| 7,402,162 B2 | 7/2008 | Ouchi | 2002/0082516 A1 | 6/2002 | Stefanchik |
| 7,404,791 B2 | 7/2008 | Linares et al. | 2002/0091391 A1 | 7/2002 | Cole et al. |
| 7,416,554 B2 | 8/2008 | Lam et al. | 2002/0095164 A1 | 7/2002 | Andreas et al. |
| 7,422,590 B2 | 9/2008 | Kupferschmid et al. | 2002/0107530 A1 | 8/2002 | Sauer et al. |
| 7,452,327 B2 | 11/2008 | Durgin et al. | 2002/0133115 A1 | 9/2002 | Gordon et al. |
| 7,455,208 B2 | 11/2008 | Wales et al. | 2002/0138086 A1 | 9/2002 | Sixto, Jr. et al. |
| 7,468,066 B2 | 12/2008 | Vargas et al. | 2002/0147456 A1 | 10/2002 | Diduch et al. |
| 7,488,295 B2 | 2/2009 | Burbank et al. | 2002/0151961 A1* | 10/2002 | Lashinski et al. ............ 623/1.15 |
| 7,497,867 B2 | 3/2009 | Lasner et al. | 2002/0183591 A1 | 12/2002 | Matsuura et al. |
| 7,507,200 B2 | 3/2009 | Okada | 2003/0023255 A1 | 1/2003 | Miles et al. |
| 7,524,281 B2 | 4/2009 | Chu et al. | 2003/0036679 A1 | 2/2003 | Kortenbach et al. |
| 7,524,302 B2 | 4/2009 | Tower | 2003/0069602 A1 | 4/2003 | Jacobs et al. |
| 7,534,228 B2 | 5/2009 | Williams | 2003/0083681 A1 | 5/2003 | Moutafis et al. |
| 7,540,872 B2 | 6/2009 | Schechter et al. | 2003/0107668 A1* | 6/2003 | Yamamoto .................... 348/357 |
| 7,544,203 B2 | 6/2009 | Chin et al. | 2003/0114732 A1 | 6/2003 | Webler et al. |
| 7,548,040 B2 | 6/2009 | Lee et al. | 2003/0120257 A1* | 6/2003 | Houston et al. ............... 604/523 |
| 7,549,564 B2 | 6/2009 | Boudreaux | 2003/0124009 A1 | 7/2003 | Ravi et al. |
| 7,553,278 B2 | 6/2009 | Kucklick | 2003/0130564 A1 | 7/2003 | Martone et al. |
| 7,553,298 B2 | 6/2009 | Hunt et al. | 2003/0130656 A1 | 7/2003 | Levin |
| 7,559,887 B2 | 7/2009 | Dannan | 2003/0158521 A1 | 8/2003 | Ameri |
| 7,559,916 B2 | 7/2009 | Smith et al. | 2003/0167062 A1 | 9/2003 | Gambale et al. |
| 7,561,916 B2 | 7/2009 | Hunt et al. | 2003/0171651 A1 | 9/2003 | Page et al. |
| 7,566,334 B2 | 7/2009 | Christian et al. | 2003/0176880 A1 | 9/2003 | Long et al. |
| 7,575,144 B2 | 8/2009 | Ortiz et al. | 2003/0191497 A1 | 10/2003 | Cope |
| 7,575,548 B2 | 8/2009 | Takemoto et al. | 2003/0195565 A1 | 10/2003 | Bonutti |
| 7,579,550 B2 | 8/2009 | Dayton et al. | 2003/0216611 A1 | 11/2003 | Vu |
| 7,582,096 B2 | 9/2009 | Gellman et al. | 2003/0216615 A1 | 11/2003 | Ouchi |
| 7,588,177 B2 | 9/2009 | Racenet | 2003/0220545 A1 | 11/2003 | Ouchi |
| 7,588,557 B2 | 9/2009 | Nakao | 2003/0225312 A1 | 12/2003 | Suzuki et al. |
| 7,618,398 B2 | 11/2009 | Holman et al. | 2003/0225332 A1 | 12/2003 | Okada et al. |
| 7,632,250 B2 | 12/2009 | Smith et al. | 2003/0229269 A1 | 12/2003 | Humphrey |
| 7,635,373 B2 | 12/2009 | Ortiz | 2003/0229371 A1 | 12/2003 | Whitworth |
| 7,651,483 B2 | 1/2010 | Byrum et al. | 2003/0236549 A1 | 12/2003 | Bonadio et al. |
| 7,651,509 B2 | 1/2010 | Bojarski et al. | 2004/0002683 A1 | 1/2004 | Nicholson et al. |
| 7,654,431 B2 | 2/2010 | Hueil et al. | 2004/0002735 A1 | 1/2004 | Lizardi et al. |
| 7,655,004 B2 | 2/2010 | Long | 2004/0034509 A1 | 2/2004 | Sauer et al. |
| 7,662,089 B2 | 2/2010 | Okada et al. | 2004/0044270 A1* | 3/2004 | Barry ........................... 600/142 |
| 7,666,180 B2 | 2/2010 | Holsten et al. | 2004/0098007 A1 | 5/2004 | Heiss |
| 7,674,259 B2 | 3/2010 | Shadduck | 2004/0101456 A1 | 5/2004 | Kuroshima et al. |
| 7,713,189 B2 | 5/2010 | Hanke | 2004/0116948 A1 | 6/2004 | Sixto, Jr. et al. |
| 7,713,270 B2 | 5/2010 | Suzuki | 2004/0127940 A1 | 7/2004 | Ginn et al. |
| 7,736,374 B2 | 6/2010 | Vaughan et al. | 2004/0133077 A1 | 7/2004 | Obenchain et al. |
| 7,744,615 B2 | 6/2010 | Couture | 2004/0133089 A1 | 7/2004 | Kilcoyne et al. |
| 7,758,577 B2 | 7/2010 | Nobis et al. | 2004/0136779 A1 | 7/2004 | Bhaskar |
| 7,762,949 B2 | 7/2010 | Nakao | 2004/0138525 A1 | 7/2004 | Saadat et al. |
| 7,762,998 B2 | 7/2010 | Birk et al. | 2004/0138529 A1 | 7/2004 | Wiltshire et al. |
| 7,771,416 B2 | 8/2010 | Spivey et al. | 2004/0138587 A1 | 7/2004 | Lyons, IV |
| 7,780,683 B2 | 8/2010 | Roue et al. | 2004/0161451 A1 | 8/2004 | Pierce et al. |
| 7,780,691 B2 | 8/2010 | Stefanchik | 2004/0182511 A1* | 9/2004 | Rakos et al. .................. 156/287 |
| 7,794,409 B2 | 9/2010 | Damarati | 2004/0186350 A1 | 9/2004 | Brenneman et al. |
| 7,794,475 B2 | 9/2010 | Hess et al. | 2004/0193009 A1 | 9/2004 | Jaffe et al. |
| 7,828,186 B2 | 11/2010 | Wales | 2004/0193146 A1 | 9/2004 | Lee et al. |
| 7,837,615 B2 | 11/2010 | Le et al. | 2004/0193186 A1 | 9/2004 | Kortenbach et al. |
| 7,846,171 B2 | 12/2010 | Kullas et al. | 2004/0193188 A1 | 9/2004 | Francese |
| 7,850,660 B2 | 12/2010 | Uth et al. | 2004/0193189 A1 | 9/2004 | Kortenbach et al. |
| 7,857,183 B2 | 12/2010 | Shelton, IV | 2004/0193200 A1 | 9/2004 | Dworschak et al. |
| 7,862,546 B2 | 1/2011 | Conlon et al. | 2004/0199051 A1* | 10/2004 | Weisel ......................... 600/141 |
| 7,867,216 B2 | 1/2011 | Wahr et al. | 2004/0199052 A1 | 10/2004 | Banik et al. |

| | | | | | |
|---|---|---|---|---|---|
| 2004/0206859 A1 | 10/2004 | Chong et al. | 2005/0277954 A1 | 12/2005 | Smith et al. |
| 2004/0210245 A1 | 10/2004 | Erickson et al. | 2005/0277955 A1 | 12/2005 | Palmer et al. |
| 2004/0215058 A1 | 10/2004 | Zirps et al. | 2005/0277956 A1 | 12/2005 | Francese et al. |
| 2004/0225183 A1 | 11/2004 | Michlitsch et al. | 2005/0277957 A1 | 12/2005 | Kuhns et al. |
| 2004/0225186 A1* | 11/2004 | Horne et al. ............... 600/139 | 2005/0283118 A1 | 12/2005 | Uth et al. |
| 2004/0230095 A1 | 11/2004 | Stefanchik et al. | 2005/0283119 A1 | 12/2005 | Uth et al. |
| 2004/0230096 A1 | 11/2004 | Stefanchik et al. | 2005/0288555 A1 | 12/2005 | Binmoeller |
| 2004/0230097 A1 | 11/2004 | Stefanchik et al. | 2006/0004406 A1 | 1/2006 | Wehrstein et al. |
| 2004/0230161 A1 | 11/2004 | Zeiner | 2006/0004409 A1 | 1/2006 | Nobis et al. |
| 2004/0249246 A1 | 12/2004 | Campos | 2006/0004410 A1 | 1/2006 | Nobis et al. |
| 2004/0249367 A1 | 12/2004 | Saadat et al. | 2006/0015009 A1 | 1/2006 | Jaffe et al. |
| 2004/0249394 A1 | 12/2004 | Morris et al. | 2006/0020167 A1 | 1/2006 | Sitzmann |
| 2004/0249443 A1* | 12/2004 | Shanley et al. ............ 623/1.15 | 2006/0020247 A1 | 1/2006 | Kagan et al. |
| 2005/0004515 A1 | 1/2005 | Hart et al. | 2006/0020334 A1* | 1/2006 | Lashinski et al. ............ 623/2.11 |
| 2005/0033265 A1* | 2/2005 | Engel et al. ................. 604/523 | 2006/0025654 A1 | 2/2006 | Suzuki et al. |
| 2005/0033277 A1 | 2/2005 | Clague et al. | 2006/0025781 A1 | 2/2006 | Young et al. |
| 2005/0033319 A1 | 2/2005 | Gambale et al. | 2006/0025812 A1 | 2/2006 | Shelton, IV |
| 2005/0033333 A1 | 2/2005 | Smith et al. | 2006/0025819 A1 | 2/2006 | Nobis et al. |
| 2005/0043690 A1 | 2/2005 | Todd | 2006/0036267 A1 | 2/2006 | Saadat et al. |
| 2005/0049616 A1 | 3/2005 | Rivera et al. | 2006/0041188 A1 | 2/2006 | Dirusso et al. |
| 2005/0065397 A1 | 3/2005 | Saadat et al. | 2006/0058582 A1 | 3/2006 | Maahs et al. |
| 2005/0065517 A1 | 3/2005 | Chin | 2006/0058776 A1 | 3/2006 | Bilsbury |
| 2005/0070754 A1 | 3/2005 | Nobis et al. | 2006/0069396 A1 | 3/2006 | Meade et al. |
| 2005/0070763 A1 | 3/2005 | Nobis et al. | 2006/0069424 A1* | 3/2006 | Acosta et al. ............... 623/1.12 |
| 2005/0070764 A1 | 3/2005 | Nobis et al. | 2006/0069425 A1 | 3/2006 | Hillis et al. |
| 2005/0080400 A1* | 4/2005 | Corcoran et al. ............ 604/523 | 2006/0074413 A1 | 4/2006 | Behzadian |
| 2005/0080413 A1 | 4/2005 | Canady | 2006/0079890 A1 | 4/2006 | Guerra |
| 2005/0085693 A1 | 4/2005 | Belson et al. | 2006/0089528 A1 | 4/2006 | Tartaglia et al. |
| 2005/0085832 A1 | 4/2005 | Sancoff et al. | 2006/0095031 A1 | 5/2006 | Ormsby |
| 2005/0090837 A1 | 4/2005 | Sixto, Jr. et al. | 2006/0095060 A1 | 5/2006 | Mayenberger et al. |
| 2005/0090838 A1 | 4/2005 | Sixto, Jr. et al. | 2006/0100687 A1* | 5/2006 | Fahey et al. ............... 623/1.11 |
| 2005/0101837 A1 | 5/2005 | Kalloo et al. | 2006/0106423 A1 | 5/2006 | Weisel et al. |
| 2005/0101838 A1 | 5/2005 | Camillocci et al. | 2006/0111209 A1 | 5/2006 | Hinman et al. |
| 2005/0107663 A1 | 5/2005 | Saadat et al. | 2006/0111210 A1 | 5/2006 | Hinman et al. |
| 2005/0107664 A1 | 5/2005 | Kalloo et al. | 2006/0111704 A1 | 5/2006 | Brenneman et al. |
| 2005/0110881 A1 | 5/2005 | Glukhovsky et al. | 2006/0129166 A1 | 6/2006 | Lavelle |
| 2005/0113847 A1 | 5/2005 | Gadberry et al. | 2006/0135962 A1 | 6/2006 | Kick et al. |
| 2005/0119613 A1 | 6/2005 | Moenning et al. | 2006/0135971 A1 | 6/2006 | Swanstrom et al. |
| 2005/0124855 A1 | 6/2005 | Jaffe et al. | 2006/0135984 A1 | 6/2006 | Kramer et al. |
| 2005/0125010 A1 | 6/2005 | Smith et al. | 2006/0142644 A1 | 6/2006 | Mulac et al. |
| 2005/0131279 A1 | 6/2005 | Boulais et al. | 2006/0142652 A1 | 6/2006 | Keenan |
| 2005/0131457 A1 | 6/2005 | Douglas et al. | 2006/0142790 A1 | 6/2006 | Gertner |
| 2005/0137454 A1 | 6/2005 | Saadat et al. | 2006/0142798 A1 | 6/2006 | Holman et al. |
| 2005/0143647 A1 | 6/2005 | Minai et al. | 2006/0149131 A1 | 7/2006 | Or |
| 2005/0143690 A1 | 6/2005 | High | 2006/0149132 A1 | 7/2006 | Iddan |
| 2005/0143774 A1 | 6/2005 | Polo | 2006/0149135 A1 | 7/2006 | Paz |
| 2005/0143803 A1* | 6/2005 | Watson et al. ............... 623/1.11 | 2006/0161190 A1 | 7/2006 | Gadberry et al. |
| 2005/0149087 A1 | 7/2005 | Ahlberg et al. | 2006/0167416 A1 | 7/2006 | Mathis et al. |
| 2005/0149096 A1 | 7/2005 | Hilal et al. | 2006/0167482 A1 | 7/2006 | Swain et al. |
| 2005/0159648 A1 | 7/2005 | Freed | 2006/0178560 A1* | 8/2006 | Saadat et al. ............... 600/114 |
| 2005/0165272 A1 | 7/2005 | Okada et al. | 2006/0183975 A1 | 8/2006 | Saadat et al. |
| 2005/0165378 A1 | 7/2005 | Heinrich et al. | 2006/0184161 A1 | 8/2006 | Maahs et al. |
| 2005/0165411 A1 | 7/2005 | Orban, III | 2006/0189844 A1 | 8/2006 | Tien |
| 2005/0165429 A1 | 7/2005 | Douglas et al. | 2006/0189845 A1 | 8/2006 | Maahs et al. |
| 2005/0177132 A1* | 8/2005 | Lentz et al. ................. 604/525 | 2006/0190027 A1 | 8/2006 | Downey |
| 2005/0182429 A1 | 8/2005 | Yamanouchi | 2006/0195084 A1 | 8/2006 | Slater |
| 2005/0192478 A1 | 9/2005 | Williams et al. | 2006/0200005 A1 | 9/2006 | Bjork et al. |
| 2005/0192598 A1 | 9/2005 | Johnson et al. | 2006/0200169 A1 | 9/2006 | Sniffin |
| 2005/0192602 A1 | 9/2005 | Manzo | 2006/0200170 A1 | 9/2006 | Aranyi |
| 2005/0192654 A1 | 9/2005 | Chanduszko et al. | 2006/0200199 A1 | 9/2006 | Bonutti et al. |
| 2005/0209557 A1* | 9/2005 | Carroll et al. ............ 604/95.04 | 2006/0217665 A1 | 9/2006 | Prosek |
| 2005/0209624 A1 | 9/2005 | Vijay | 2006/0217697 A1 | 9/2006 | Lau et al. |
| 2005/0215858 A1 | 9/2005 | Vail, III | 2006/0217742 A1 | 9/2006 | Messerly et al. |
| 2005/0216050 A1 | 9/2005 | Sepetka et al. | 2006/0217743 A1 | 9/2006 | Messerly et al. |
| 2005/0228406 A1 | 10/2005 | Bose | 2006/0229639 A1 | 10/2006 | Whitfield |
| 2005/0234297 A1 | 10/2005 | Devierre et al. | 2006/0229640 A1 | 10/2006 | Whitfield |
| 2005/0250983 A1 | 11/2005 | Tremaglio et al. | 2006/0237022 A1 | 10/2006 | Chen et al. |
| 2005/0250990 A1 | 11/2005 | Le et al. | 2006/0237023 A1 | 10/2006 | Cox et al. |
| 2005/0250993 A1 | 11/2005 | Jaeger | 2006/0241570 A1 | 10/2006 | Wilk |
| 2005/0251166 A1 | 11/2005 | Vaughan et al. | 2006/0247576 A1 | 11/2006 | Poncet |
| 2005/0251176 A1 | 11/2005 | Swanstrom et al. | 2006/0247673 A1 | 11/2006 | Voegele et al. |
| 2005/0261674 A1 | 11/2005 | Nobis et al. | 2006/0253004 A1 | 11/2006 | Frisch et al. |
| 2005/0267492 A1 | 12/2005 | Poncet et al. | 2006/0253039 A1 | 11/2006 | McKenna et al. |
| 2005/0272975 A1 | 12/2005 | McWeeney et al. | 2006/0258907 A1 | 11/2006 | Stefanchik et al. |
| 2005/0272977 A1 | 12/2005 | Saadat et al. | 2006/0258908 A1 | 11/2006 | Stefanchik et al. |
| 2005/0273084 A1 | 12/2005 | Hinman et al. | 2006/0258910 A1 | 11/2006 | Stefanchik et al. |
| 2005/0277945 A1 | 12/2005 | Saadat et al. | 2006/0258954 A1 | 11/2006 | Timberlake et al. |
| 2005/0277951 A1 | 12/2005 | Smith et al. | 2006/0258955 A1 | 11/2006 | Hoffman et al. |
| 2005/0277952 A1 | 12/2005 | Arp et al. | 2006/0259010 A1 | 11/2006 | Stefanchik et al. |

| | | | | | | |
|---|---|---|---|---|---|---|
| 2006/0264752 A1 | 11/2006 | Rubinsky et al. | | 2007/0260121 A1 | 11/2007 | Bakos et al. |
| 2006/0264904 A1* | 11/2006 | Kerby et al. ............... 604/523 | | 2007/0260273 A1 | 11/2007 | Cropper et al. |
| 2006/0264930 A1 | 11/2006 | Nishimura | | 2007/0270629 A1 | 11/2007 | Charles |
| 2006/0270902 A1 | 11/2006 | Igarashi et al. | | 2007/0270889 A1 | 11/2007 | Conlon et al. |
| 2006/0271102 A1 | 11/2006 | Bosshard et al. | | 2007/0270895 A1 | 11/2007 | Nobis et al. |
| 2006/0276835 A1 | 12/2006 | Uchida | | 2007/0270907 A1 | 11/2007 | Stokes et al. |
| 2006/0281970 A1 | 12/2006 | Stokes et al. | | 2007/0282371 A1 | 12/2007 | Lee et al. |
| 2006/0282106 A1 | 12/2006 | Cole et al. | | 2007/0293727 A1 | 12/2007 | Goldfarb et al. |
| 2006/0285732 A1 | 12/2006 | Horn et al. | | 2007/0299387 A1 | 12/2007 | Williams et al. |
| 2006/0287644 A1 | 12/2006 | Inganas et al. | | 2008/0004650 A1 | 1/2008 | George |
| 2006/0287666 A1 | 12/2006 | Saadat et al. | | 2008/0015409 A1 | 1/2008 | Barlow et al. |
| 2006/0293626 A1 | 12/2006 | Byrum et al. | | 2008/0015552 A1 | 1/2008 | Doyle et al. |
| 2007/0002135 A1 | 1/2007 | Glukhovsky | | 2008/0021416 A1 | 1/2008 | Arai et al. |
| 2007/0005019 A1 | 1/2007 | Okishige | | 2008/0022927 A1 | 1/2008 | Zhang et al. |
| 2007/0010801 A1 | 1/2007 | Chen et al. | | 2008/0027387 A1 | 1/2008 | Grabinsky |
| 2007/0015965 A1 | 1/2007 | Cox et al. | | 2008/0033451 A1 | 2/2008 | Rieber et al. |
| 2007/0016225 A1 | 1/2007 | Nakao | | 2008/0051629 A1 | 2/2008 | Sugiyama et al. |
| 2007/0032700 A1 | 2/2007 | Fowler et al. | | 2008/0051735 A1 | 2/2008 | Measamer et al. |
| 2007/0032701 A1 | 2/2007 | Fowler et al. | | 2008/0058586 A1 | 3/2008 | Karpiel |
| 2007/0043261 A1* | 2/2007 | Watanabe et al. ............. 600/144 | | 2008/0065169 A1 | 3/2008 | Colliou et al. |
| 2007/0043345 A1 | 2/2007 | Davalos et al. | | 2008/0071264 A1 | 3/2008 | Azure |
| 2007/0049800 A1 | 3/2007 | Boulais | | 2008/0086172 A1 | 4/2008 | Martin et al. |
| 2007/0049902 A1* | 3/2007 | Griffin et al. ............... 604/523 | | 2008/0097159 A1 | 4/2008 | Ishiguro |
| 2007/0051375 A1 | 3/2007 | Milliman | | 2008/0097472 A1 | 4/2008 | Agmon et al. |
| 2007/0060880 A1 | 3/2007 | Gregorich et al. | | 2008/0097483 A1 | 4/2008 | Ortiz et al. |
| 2007/0067017 A1* | 3/2007 | Trapp ............................ 623/1.16 | | 2008/0103527 A1 | 5/2008 | Martin et al. |
| 2007/0073102 A1 | 3/2007 | Matsuno et al. | | 2008/0114384 A1 | 5/2008 | Chang et al. |
| 2007/0073269 A1 | 3/2007 | Becker | | 2008/0119870 A1 | 5/2008 | Williams |
| 2007/0079924 A1 | 4/2007 | Saadat et al. | | 2008/0119891 A1 | 5/2008 | Miles et al. |
| 2007/0088370 A1 | 4/2007 | Kahle et al. | | 2008/0125796 A1 | 5/2008 | Graham |
| 2007/0100375 A1 | 5/2007 | Mikkaichi et al. | | 2008/0132892 A1 | 6/2008 | Lunsford et al. |
| 2007/0100376 A1 | 5/2007 | Mikkaichi et al. | | 2008/0139882 A1 | 6/2008 | Fujimori |
| 2007/0106118 A1 | 5/2007 | Moriyama | | 2008/0147113 A1 | 6/2008 | Nobis et al. |
| 2007/0112251 A1 | 5/2007 | Nakhuda | | 2008/0171907 A1 | 7/2008 | Long et al. |
| 2007/0112331 A1 | 5/2007 | Weber et al. | | 2008/0177135 A1 | 7/2008 | Muyari et al. |
| 2007/0112342 A1 | 5/2007 | Pearson et al. | | 2008/0188868 A1 | 8/2008 | Weitzner et al. |
| 2007/0112383 A1 | 5/2007 | Conlon et al. | | 2008/0200755 A1 | 8/2008 | Bakos |
| 2007/0112384 A1 | 5/2007 | Conlon et al. | | 2008/0200762 A1 | 8/2008 | Stokes et al. |
| 2007/0112385 A1 | 5/2007 | Conlon | | 2008/0200911 A1 | 8/2008 | Long |
| 2007/0112417 A1* | 5/2007 | Shanley et al. ............... 623/1.16 | | 2008/0200933 A1 | 8/2008 | Bakos et al. |
| 2007/0112425 A1 | 5/2007 | Schaller et al. | | 2008/0200934 A1 | 8/2008 | Fox |
| 2007/0118115 A1 | 5/2007 | Artale et al. | | 2008/0208213 A1 | 8/2008 | Benjamin et al. |
| 2007/0123840 A1 | 5/2007 | Cox | | 2008/0221587 A1 | 9/2008 | Schwartz |
| 2007/0129605 A1 | 6/2007 | Schaaf | | 2008/0221619 A1 | 9/2008 | Spivey et al. |
| 2007/0129719 A1 | 6/2007 | Kendale et al. | | 2008/0228213 A1 | 9/2008 | Blakeney et al. |
| 2007/0129760 A1 | 6/2007 | Demarais et al. | | 2008/0230972 A1 | 9/2008 | Ganley |
| 2007/0135709 A1 | 6/2007 | Rioux et al. | | 2008/0234696 A1 | 9/2008 | Taylor et al. |
| 2007/0135803 A1 | 6/2007 | Belson | | 2008/0243106 A1 | 10/2008 | Coe et al. |
| 2007/0142706 A1 | 6/2007 | Matsui et al. | | 2008/0243148 A1 | 10/2008 | Mikkaichi et al. |
| 2007/0142780 A1 | 6/2007 | Van Lue | | 2008/0243176 A1 | 10/2008 | Weitzner et al. |
| 2007/0154460 A1 | 7/2007 | Kraft et al. | | 2008/0249567 A1 | 10/2008 | Kaplan |
| 2007/0156028 A1 | 7/2007 | Van Lue et al. | | 2008/0262540 A1 | 10/2008 | Bangera et al. |
| 2007/0156127 A1 | 7/2007 | Rioux et al. | | 2008/0269782 A1 | 10/2008 | Stefanchik et al. |
| 2007/0161855 A1 | 7/2007 | Mikkaichi et al. | | 2008/0269783 A1 | 10/2008 | Griffith |
| 2007/0162101 A1 | 7/2007 | Burgermeister et al. | | 2008/0275474 A1 | 11/2008 | Martin et al. |
| 2007/0173691 A1 | 7/2007 | Yokoi et al. | | 2008/0275475 A1 | 11/2008 | Schwemberger et al. |
| 2007/0173869 A1 | 7/2007 | Gannoe et al. | | 2008/0287737 A1 | 11/2008 | Dejima |
| 2007/0173870 A2 | 7/2007 | Zacharias | | 2008/0287983 A1 | 11/2008 | Smith et al. |
| 2007/0173872 A1 | 7/2007 | Neuenfeldt | | 2008/0300461 A1 | 12/2008 | Shaw et al. |
| 2007/0179525 A1 | 8/2007 | Frecker et al. | | 2008/0300547 A1 | 12/2008 | Bakos |
| 2007/0179530 A1 | 8/2007 | Tieu et al. | | 2008/0309758 A1 | 12/2008 | Karasawa et al. |
| 2007/0197865 A1 | 8/2007 | Miyake et al. | | 2008/0312496 A1 | 12/2008 | Zwolinski |
| 2007/0198057 A1 | 8/2007 | Gelbart et al. | | 2008/0312499 A1 | 12/2008 | Handa et al. |
| 2007/0203487 A1 | 8/2007 | Sugita | | 2008/0312500 A1 | 12/2008 | Asada et al. |
| 2007/0208336 A1 | 9/2007 | Kim et al. | | 2008/0312506 A1 | 12/2008 | Spivey et al. |
| 2007/0208364 A1 | 9/2007 | Smith et al. | | 2008/0319436 A1 | 12/2008 | Daniel et al. |
| 2007/0213754 A1 | 9/2007 | Mikkaichi et al. | | 2008/0319439 A1 | 12/2008 | Ootsubu |
| 2007/0225554 A1 | 9/2007 | Maseda et al. | | 2009/0054728 A1 | 2/2009 | Trusty |
| 2007/0233040 A1 | 10/2007 | Macnamara et al. | | 2009/0062788 A1 | 3/2009 | Long et al. |
| 2007/0244358 A1 | 10/2007 | Lee | | 2009/0062792 A1 | 3/2009 | Vakharia et al. |
| 2007/0250038 A1 | 10/2007 | Boulais | | 2009/0062795 A1 | 3/2009 | Vakharia et al. |
| 2007/0250057 A1 | 10/2007 | Nobis et al. | | 2009/0069634 A1 | 3/2009 | Larkin |
| 2007/0255096 A1 | 11/2007 | Stefanchik et al. | | 2009/0076499 A1 | 3/2009 | Azure |
| 2007/0255100 A1 | 11/2007 | Barlow et al. | | 2009/0078736 A1 | 3/2009 | Van Lue |
| 2007/0255273 A1 | 11/2007 | Fernandez et al. | | 2009/0082776 A1 | 3/2009 | Cresina |
| 2007/0255303 A1 | 11/2007 | Bakos et al. | | 2009/0082779 A1 | 3/2009 | Nakao |
| 2007/0255306 A1 | 11/2007 | Conlon et al. | | 2009/0112059 A1 | 4/2009 | Nobis |
| 2007/0260112 A1 | 11/2007 | Rahmani | | 2009/0112062 A1 | 4/2009 | Bakos |
| 2007/0260117 A1 | 11/2007 | Zwolinski et al. | | 2009/0112063 A1 | 4/2009 | Bakos et al. |

| Publication No. | Date | Inventor |
|---|---|---|
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |
| 2012/0004502 A1 | 1/2012 | Weitzner et al. |
| 2012/0088965 A1 | 4/2012 | Stokes et al. |
| 2012/0089089 A1 | 4/2012 | Swain et al. |
| 2012/0089093 A1 | 4/2012 | Trusty |

FOREIGN PATENT DOCUMENTS

| | | |
|---|---|---|
| DE | 3008120 A1 | 9/1980 |
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |

| | | | |
|---|---|---|---|
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A1 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

K. Sumiyama et al., "Endoscopic Caps," Tech. Gastrointest. Endosc., vol. 8, pp. 28-32, 2006.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Feb. 1826. Recueil De La Societe Royale De Medecin De Marseille. Marseille: Impr. D'Achard, 1826; 1:127-31. (with English translation).
Printout of web page—http://www.vacumed.com/zcom/product/Product.do?compid=27&prodid=852,#51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ECRP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D. . ., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal Notes Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/694,452, filed Jan. 27, 2010.
U.S. Appl. No. 12/752,701, filed Apr. 1, 2010.
U.S. Appl. No. 11/796,035, filed Apr. 26, 2007.
U.S. Appl. No. 11/981,134, filed Oct. 31, 2007.

United States Patent Application entitled Endoscopic Translumenal Flexible Overtube, filed Jul. 14, 2008.

United States Patent Application entitled Tissue Apposition Clip Application Devices and Methods, filed Jul. 14, 2008.

Michael S. Kavic, M.D., "Natural Orifice Translumenal Endoscopic Surgery: "NOTES"", JSLS, vol. 10, pp. 133-134 (2006).

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

"Z-Offset Technique Used in the Introduction of Trocar During Laparoscopic Surgery," M.S. Hershey NOTES Presentation to EES NOTES Development Team, Sep. 27, 2007.

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastomosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

U.S. Appl. No. 11/437,440, filed May 19, 2006.
U.S. Appl. No. 11/274,352, filed Nov. 15, 2005.
U.S. Appl. No. 11/744,271, filed May 4, 2007.
U.S. Appl. No. 11/744,279, filed May 4, 2007.
U.S. Appl. No. 11/437,864, filed May 19, 2006.
U.S. Appl. No. 11/274,358, filed Nov. 15, 2005.
U.S. Appl. No. 11/274,354, filed Nov. 15, 2005.
U.S. Appl. No. 11/706,685, filed Feb. 15, 2007.
U.S. Appl. No. 11/706,460, filed Feb. 15, 2007.
U.S. Appl. No. 11/706,591, filed Feb. 15, 2007.
U.S. Appl. No. 11/706,766, filed Feb. 15, 2007.
U.S. Appl. No. 11/706,811, filed Feb. 15, 2007.
U.S. Appl. No. 11/715,710, filed Mar. 8, 2007.
U.S. Appl. No. 11/796,357, filed Apr. 27, 2007.
U.S. Appl. No. 11/894,358, filed Aug. 21, 2007.
U.S. Appl. No. 11/986,084, filed Nov. 20, 2007.
U.S. Appl. No. 12/014,417, filed Jan. 5, 2008.
U.S. Appl. No. 11/981,070, filed Oct. 31, 2007.
U.S. Appl. No. 11/968,810, filed Jan. 3, 2008.
U.S. Appl. No. 11/981,078, filed Oct. 31, 2007.
U.S. Appl. No. 11/998,370, filed Nov. 29, 2007.
U.S. Appl. No. 11/986,420, filed Nov. 21, 2007.
U.S. Appl. No. 12/019,461, filed Jan. 24, 2008.
U.S. Appl. No. 11/897,676, filed Aug. 31, 2007.
U.S. Appl. No. 12/109,673, filed Apr. 25, 2008.
U.S. Appl. No. 12/109,699, filed Apr. 25, 2008.
U.S. Appl. No. 11/986,489 filed Nov. 21, 2007.
U.S. Appl. No. 12/115,916, filed May 6, 2008.
U.S. Appl. No. 12/045,318, filed Mar. 10, 2008.
U.S. Appl. No. 11/707,831, filed Feb. 16, 2007.
U.S. Appl. No. 12/122,031, filed May 16, 2008.
U.S. Appl. No. 12/170,862, filed Jul. 10, 2008.
U.S. Appl. No. 12/133,109, filed Jun. 4, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/129,784, filed May 30, 2008.
U.S. Appl. No. 12/130,652, filed May 30, 2008.
U.S. Appl. No. 12/163,255, filed Jun. 27, 2008.
U.S. Appl. No. 12/129,880, filed May 30, 2008.
U.S. Appl. No. 12/133,953, filed Jun. 5, 2008.
U.S. Appl. No. 12/169,868, filed Jul. 9, 2008.

Zadno et al., "Linear Superelasticity in Cold-Worked NI-TI," Engineering Aspects of Shape Memory Alloys, pp. 414-419 (1990).

U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.

Ethicon, Inc., "Wound Closure Manual: Chapter 3 (The Surgical Needle)," 15 pages, (1994).

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles./view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).

Jolly et al., Properties and Applications of Commercial Magnetorheological Fluids. SPIE 5th Annual Int. Symposium on Smart Structures and Materials, 1998 (18 pages).

U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

* cited by examiner

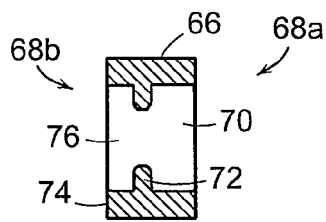
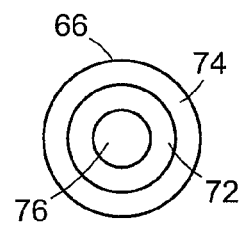
FIG. 7A          FIG. 7B
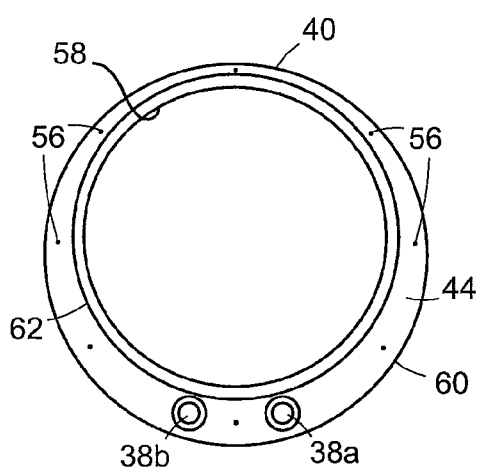
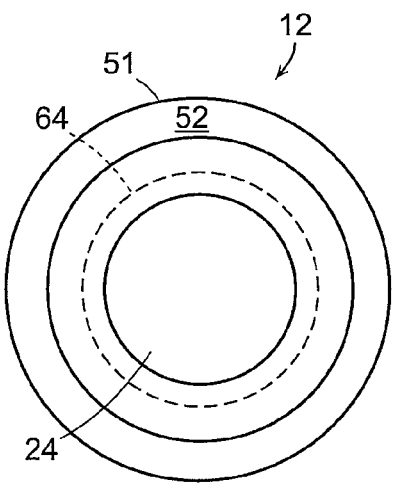
FIG. 4          FIG. 6
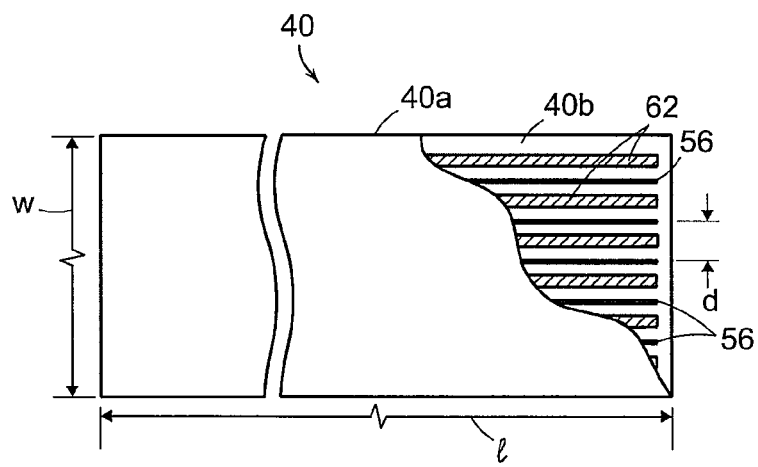
FIG. 5

ENDOSCOPIC TRANSLUMENAL ARTICULATABLE STEERABLE OVERTUBE

BACKGROUND

In laparoscopic surgical procedures, a small incision is made in the body. A trocar is inserted through the incision. The trocar receives an elongate shaft of a surgical device to position a distal end of the shaft at a surgical worksite. In some endoscopic procedures, the elongate shaft of the surgical device is inserted through a natural orifice of the patient, such as the mouth, vagina, or anus, and is advanced along an internal pathway to position the distal end of the device at the surgical worksite. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Endoscopic surgery can be used to access the abdominal cavity via natural openings (mouth, anus, vagina, urethra) of the body and through the peritoneal lining of the abdominal cavity. The size and shape of instruments that may be passed through a body lumen to perform a medical procedure in the abdominal cavity are greatly restricted due to the anatomical properties of the lumen. General surgeons, gastroenterologists, and other medical specialists, routinely use flexible endoscopes for intralumenal (within the lumen of the alimentary canal) examination and treatment of the upper gastrointestinal (GI) tract, via the mouth, and the lower GI tract, via the anus. In these procedures, the physician pushes the flexible endoscopes into the lumen, periodically pausing to articulate the distal end of the endoscope. In this manner, the physician may navigate the crooked passageway of the upper GI past the pharynx, through the esophagus and gastroesophageal junction, and into the stomach. In the process, the physician must take great care not to injure the delicate mucosal lining of the lumen, which has a non-circular cross sectional configuration when relaxed, but can stretch open to a diameter in the range of about 15-25 mm during the insertion procedure.

During translumenal procedures, a puncture must be formed in the stomach wall, gastrointestinal tract, or other epithelialized natural orifice to access the peritoneal cavity. A needle knife is one device often used to form such a puncture. The needle knife is inserted through the working channel of the endoscope and utilizes energy to penetrate through the tissue. A guidewire is then feed through the endoscope and is passed through the puncture in the stomach wall and into the peritoneal cavity. When the needle knife is removed, the guidewire is left as a placeholder. A balloon catheter is then passed over the guidewire through the working channel of the endoscope to position the balloon within the opening in the stomach wall. The balloon is inflated to increase the size of the opening, thereby enabling the endoscope to push against the rear of the balloon and to be feed through the dilated opening and into the peritoneal cavity. Once the endoscope is positioned within the peritoneal cavity, numerous procedures can be performed with instruments introduced through the one or more working channels of the endoscope.

While current methods and devices used to articulate and steer flexible endoscopes into a natural orifice of a patient are effective, there are no articulatable steerable flexible cannulas or trocars that are sufficiently flexible for receiving an endoscope while simultaneously having sufficient column strength for inserting into internal body lumens or cavities. Traditional overtubes that slide over the endoscope generally are not sufficiently flexible, articulatable or steerable, and do not have sufficient column strength to be inserted into internal body lumens or cavities, such as the peritoneal cavity.

Accordingly, there remains a need for improved endoscopic translumenal methods and devices.

BRIEF DESCRIPTION OF THE DRAWINGS

The various embodiments will be more fully understood from the following detailed description taken in conjunction with the accompanying drawings, in which:

FIG. 4 is cross-sectional view of one embodiment of the flexible sheath portion of the flexible overtube taken along section line 4-4 as shown in FIG. 2.

FIG. 5 is a partial cut-away view of one embodiment of the flexible sheath to show a method of fabricating the flexible sheath.

FIG. 6 is a distal end view of one embodiment of the flexible overtube shown in FIG. 2.

FIG. 7A is a cross-sectional view of one embodiment of the endoscopic end cap.

FIG. 7B is a distal end view of one embodiment of the endoscopic end cap.

FIG. 10A illustrates one embodiment of a flexible endoscopic shaft of an endoscope inserted inside a stomach wall and a distal end of the endoscopic end cap positioned in contact with an internal portion of the stomach wall.

FIG. 10N shows one embodiment of a flexible central needle in a fully extended configuration.

DESCRIPTION

Methods and devices are provided for a flexible endoscopic translumenal overtube for receiving a flexible endoscope therethrough. Certain embodiments of a flexible endoscopic translumenal overtube will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting example embodiments and that the scope of the embodiments described in this application is defined solely by the claims. The features illustrated or described in connection with one embodiment may be combined with the features of other embodiments. Such modifications and variations are intended to be included within the scope of this application.

It will be appreciated that the terms "proximal" and "distal" are used herein with reference to a clinician manipulating one end of an instrument that protrudes out of a natural orifice (or opening) of the patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the drawings. However, surgical instruments may be used in many orientations and positions, and these terms are not intended to be limiting and absolute.

Figure 1:
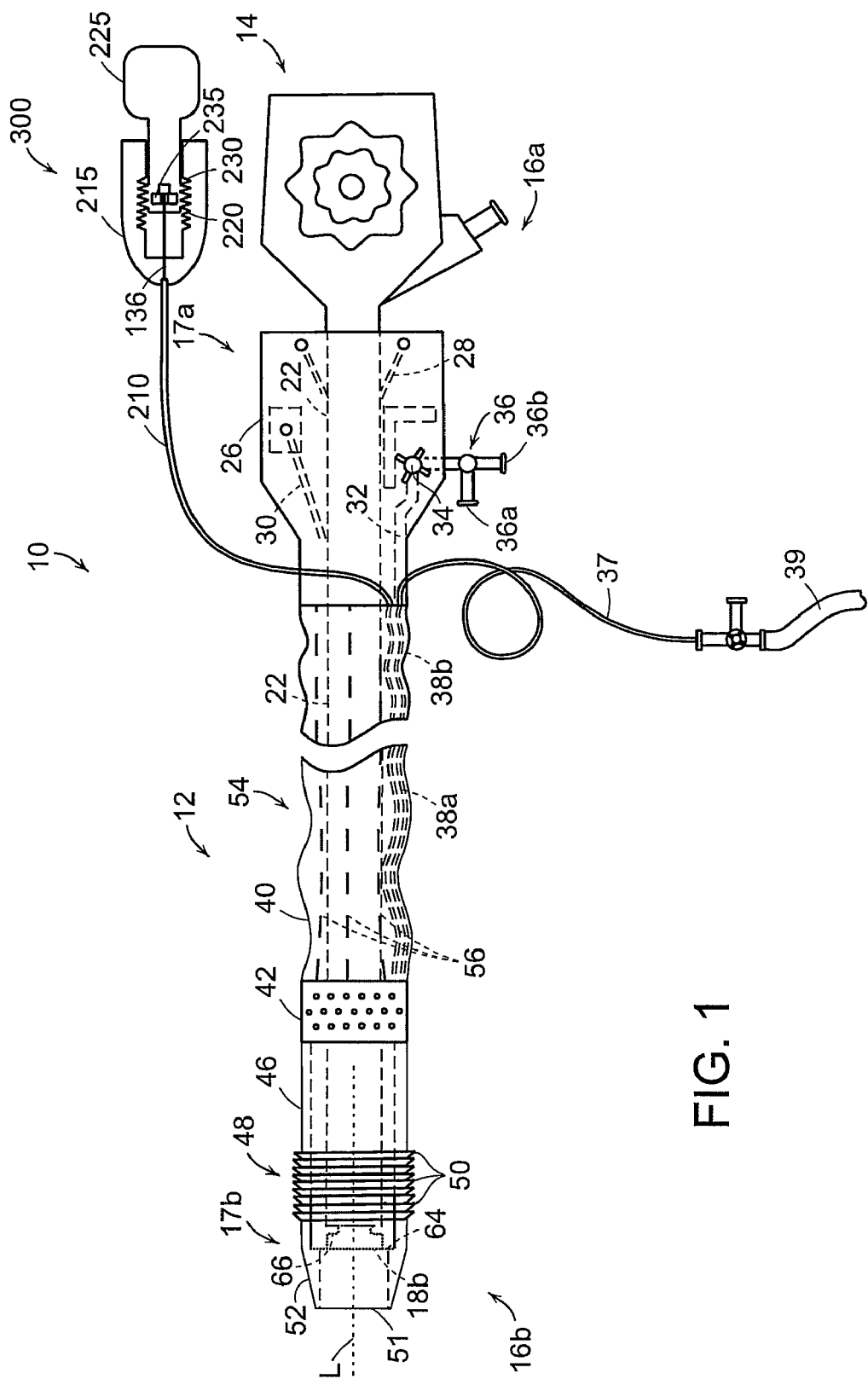
FIG. 1 is a side view of one embodiment of a flexible endoscopic translumenal overtube assembly comprising a flexible endoscope disposed within one embodiment of a flexible overtube.
Figure 2:
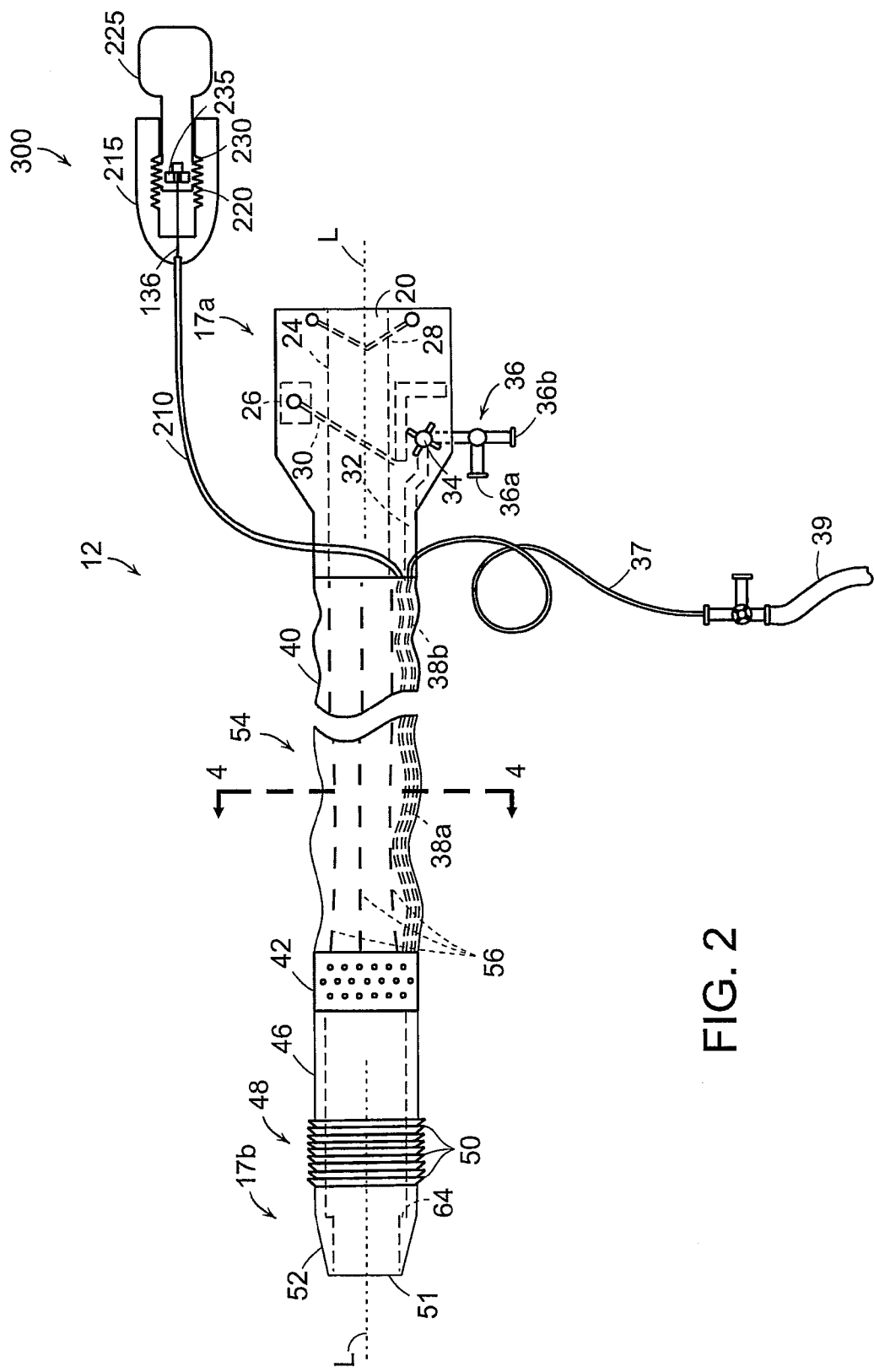
FIG. 2 is a side view of one embodiment the flexible overtube of the assembly shown in FIG. 1.
Figure 3:
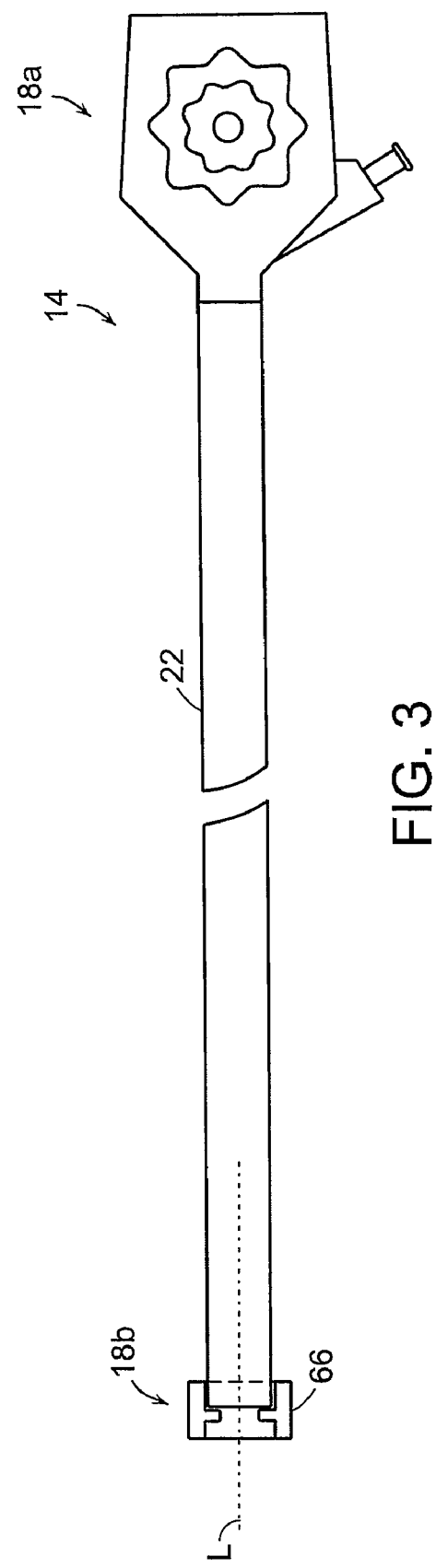
FIG. 3 is a side view of one embodiment of the endoscope of the assembly shown in FIG. 1.

FIG. 1 is a side view of one embodiment of a flexible endoscopic translumenal overtube assembly 10 comprising a flexible endoscope 14 disposed within a flexible overtube 12. The flexible endoscopic translumenal overtube assembly 10 extends substantially along a longitudinal axis "L." FIG. 2 is a side view of the flexible overtube 12 of the assembly 10 shown in FIG. 1. The flexible overtube 12 is coupled to a steerable segment 46 that is coupled to an actuation handle 300 for actively articulating the steerable segment 46 away from a neutral axis, e.g., the longitudinal axis "L," in a radius of curvature defined by a pattern or series of cuts formed on a steerable element of the steerable segment 46. FIG. 3 is a side view of the endoscope 14 portion of the assembly 10 shown in FIG. 1. With reference to FIGS. 1-3, in one embodiment, the endoscopic translumenal overtube assembly 10 comprises a proximal end 16a and a distal end 16b. The proximal end 16a remains out of the patient and the distal end 16b is inserted through a natural orifice, such as the mouth, vagina, or anus, and is advanced along a pathway to position a distal end of the device at a surgical site. The flexible overtube 12 comprises a flexible hollow body having a proximal end 17a and a distal end 17b and defining an opening 24 extending therebetween. The endoscope 14 also comprises a proximal end 18a and a distal end 18b. The distal end 18b of the endoscope 14 is slidably introduced into an opening 20 defined at the proximal end 16a of the flexible overtube 12. The distal end 18b of the endoscope 14 is inserted through the proximal opening 20 of the flexible overtube 12. The distal end 18b and a flexible shaft 22 portion of the endoscope 14 are advanced through the opening 24 defined by the flexible overtube 12 until the distal end 18b of the endoscope 14 engages the distal end 17b of the flexible overtube 12, as discussed in more detail below. A middle segment 54 of the flexible overtube 12 comprises a flexible sheath 40 defining an opening along the longitudinal axis "L" suitably sized to receive the flexible shaft 22 of the endoscope 14 with some clearance for insufflation. The flexible sheath 40 is formed into a longitudinally extending tube such that the outside diameter 60 (FIG. 4) of the flexible sheath 40 can be minimized to a suitable dimension required to pass through a desired anatomical lumen or body cavity. The flexible shaft 22 of the endoscope 14 can be moved independently of the flexible sheath 40. The flexible sheath 40 can be left in place in the anatomical lumen as a conduit for reintroducing therein the flexible shaft 22 of the endoscope 14 or for introducing therein other instruments for use within the anatomical lumen or body cavity. The endoscope 14 comprises one or more working channels to introducing various surgical instruments to the surgical worksite within the patient.

With reference to FIGS. 1 and 2, in one embodiment the proximal end 17a of the flexible overtube 12 comprises a seal system 26 to provide a fluid tight seal regardless of whether the endoscope 14 is located within the flexible overtube 12. It will be appreciated that a fluid tight seal refers to a seal sufficient to maintain pneumoperitoneum fluid pressure with incidental gaseous or fluid leakage. In one embodiment, at least one fluid tight seal 28 is provided at the proximal end 17a of the flexible overtube 12. The at least one fluid tight seal 28 prevents leakage of fluids around the flexible shaft 22 portion of the endoscope 14 positioned within the flexible overtube 12. In one embodiment, an additional fluid tight seal 30 may be provided near the proximal end 17a of the flexible overtube 12 to prevent leakage of fluid through the inside of the flexible overtube 12 when the opening 24 is free of devices, such as the endoscope 14. The first and second seals 28, 30 may have a variety of configurations. In various embodiments, however, the first and second seals 28, 30 may be configured to provide fluid tight seals around an endoscope having a size range between about 5 mm to about 13 mm. In other embodiments, the first and second seals 28, 30 may be configured to provide suitable fluid tight seals around endoscopes having other sizes. Therefore, the embodiments should not be limited in this context.

In one embodiment, the proximal end 17a of the flexible overtube 12 comprises an opening 32 distal to the first and second seals 28, 30. The opening 32 can be selectively opened and closed to allow passage of fluids from inside the flexible overtube 12 to the outside of the flexible overtube 12. The opening 32 is fluidically coupled to a valve 34 to enable the opening to fluidically couple to a fluid connection 36. The valve 34 may have a variety of configurations, and in the illustrated embodiment is a stopcock type valve. The fluid connection 36 is configured with one or more fluid ports 36a, 36b to fluidically couple either a positive pressure source (e.g., insufflation source) or a negative pressure source (e.g., suction source) to the flexible overtube 12. The first fluid port 36a is fluidically coupled to the interior of the flexible sheath 40 portion of the flexible overtube 12. The first fluid port 36a also may be fluidically coupled to an insufflation system suitable for insufflating and maintaining pneumoperitoneum fluid pressure within the peritoneal cavity during a surgical or diagnostic procedure. The first and second seals 28, 30 provide fluid tight seals to maintain the pneumoperitoneum fluid pressure to prevent the peritoneal cavity from deflating during the procedure. The first fluid port 36a may be a luer connection to couple to a syringe or insufflator. In one embodiment, the first fluid port 36a may be a female luer connection.

First and second lumens 38a, 38b are embedded within the flexible sheath 40 portion of the flexible overtube 12 and are fluidically separated from each other and from the interior of flexible sheath 40. In one embodiment, the first lumen 38a forms a conduit from the proximal end of the flexible overtube 12 to the steerable segment 46. In one embodiment, the first lumen 38a is sized to receive a pull cable 136 suitable for actuating the steerable segment 46. The pull cable 136 may be contained within a coil pipe assembly 210 used in the actuation of the steerable segment 46, as described with particularity below. In one embodiment, the second lumen 38b is fluidically coupled to a suction collar 42, which is in fluid communication with the exterior surface of the flexible sheath 40. The proximal end of the second lumen 38b is fluidically coupled to a suction source via flexible tubing 37. The flexible tubing 37 may be coupled to an endoscope, syringe, or positive or negative pressure source via a flexible tubing 39. The suction collar 42 can be used to evacuate the inside of an organ while the distal end 17b of flexible overtube 12 is positioned through the wall of the organ. This may be particularly useful in procedures where the distal end 17b of the flexible overtube 12 is positioned in the stomach, which may balloon to a size that may hinder the procedure. With the flexible tubing 39 coupled to a negative pressure source, the clinician may deflate the organ through the suction collar 42 without repositioning the flexible overtube 12.

The distal end 17b of the flexible overtube 12 may comprise a tapered segment 52, which provides a smooth transition while passing through an internal lumen or a dilated orifice formed in the tissue wall of an organ. A tissue gripping stability feature 48 may be formed near the distal end 17b of the flexible overtube 12 on an exterior surface thereof. The stability feature 48 helps position the distal end 17b of the flexible overtube 12 in the patient's body, e.g., the penetrated tissue wall of an organ. The stability feature 48 is configured to allow the distal end 17b of the flexible overtube 12 to easily pass through a dilated orifice formed through the tissue wall of an organ and provides tissue gripping features to prevent the distal end 17b from being easily pulled back through the dilated orifice in the tissue wall of the organ. The stability feature 48 may have a variety of configurations. In the illustrated embodiment, the stability feature 48 comprises a plurality of annular rings 50 formed on the outer surface of the flexible overtube 12. In the illustrated embodiment, the annular rings 50 have a triangular cross section. In other embodiments, the stability feature 48 may comprise a balloon disposed on the outer surface of the flexible overtube 12 that allows easy passage through a tissue wall when deflated and maintains the position of the distal end 17b of the flexible overtube 12 when inflated.

The actuation handle 300 is used to apply tension to the pull cable 136 to bend the steerable segment 46. The actuation handle 300 comprises a housing 215 including internal threads 220 on its interior surface, and a knob 225 containing mating threads 230 on its external surface. The pull cable 136 is fixed to the knob 225 through a rotational coupling 235 and the coil pipe 210 is fixed to the housing 215. Clockwise rotation of the knob 225 results in translation of the knob 225 relative to the housing 215 and applies tension to the pull cable 136. Rotation is continued until the tension in the pull cable 136 creates the desired amount of angulation off of the neutral axis "L" of the steerable segment 46. The actuation handle 300 may then be placed aside during a portion of the procedure with the steerable segment 46 remaining in its flexed state. When desired, the knob 225 can then be rotated counterclockwise to reduce tension in the pull cable 136, allowing the steerable segment 46 to return to a straight position.

FIG. 4 is cross-sectional view of the flexible sheath 40 portion of the flexible overtube 12 taken along section line 4-4 as shown in FIG. 2. The fluid tight first and second lumens 38a, b are embedded within a wall 44 portion of the flexile sheath 40 and extend along the length of the flexible overtube 12. The embedded lumens 38a, b may have a variety of configurations. In one embodiment, the first and second lumens 38a, b may be made of coil pipes for flexibility and may be coated with a polyethylene (PET) coating. In one embodiment, the inner diameter of each of the embedded lumens 38a, b may be about 1 mm. In one embodiment, a distal end of the second lumen 38b is fluidically coupled to the suction collar 42. Accordingly, the suction collar 42 may be used to draw fluid from the inside of a patient's body and into the fluid tight second lumen 38b when the proximal end of the second lumen 38b is connected to a negative pressure source via the flexible tubing 39. In other embodiments, the first and second lumen 38a, b each may be configured to receive the pull cable 136 within the elongate hollow portion of the embedded lumen.

With reference now to FIGS. 1-4, in one embodiment the middle segment 54 of the flexible overtube 12 is located between the proximal and distal ends 17 a, b. The middle segment 54 may have a variety of configurations. In the illustrated embodiment the middle segment 54 comprises the flexible sheath 40 sized to fit comfortably over the flexible shaft 22 of the endoscope 14. In one embodiment, the flexible sheath 40 may be formed of any suitable sheath material having a minimal wall thickness but with sufficient strength and toughness to resist tears and punctures when introduced over the flexible shaft 22. The sheath material also should be leak proof, biocompatible, lubricious (e.g., slippery, low friction), and should provide a fluid tight barrier between the flexible shaft 22 of the endoscope 14 and the internal body lumen in which the flexible overtube is inserted. In one embodiment, the flexible sheath 40 may be formed of TYVEK®. Those skilled in the art will appreciate that TYVEK® material can be configured to form a fluid tight barrier, is highly rip resistant, biocompatible, and is naturally lubricious.

In one embodiment, the flexible sheath 40 may comprise longitudinally disposed reinforcing structural members 56 disposed along the length of the flexible sheath 40. The structural members 56 provide columnar strength to the flexile sheath 40 to assist in the independent movement of the flexible shaft 22 of the endoscope 14 relative to the flexible sheath 40. Although the reinforcing structural members 56 can have a variety of configurations, in one embodiment, the reinforcing structural members 56 in the illustrated embodiment are configured as longitudinally extending spaced apart elongate wires. In one embodiment, the flexible sheath 40 may comprise an inner surface 58 which may define the inner diameter of the flexible sheath 40.

FIG. 5 is a partial cut-away view of one embodiment of the flexible sheath 40 to show a method of fabricating the flexible sheath 40. As illustrated, the flexible sheath 40 comprises a first layer 40 a and a second layer 40 b. The first and second layers 40 a, b have a suitable length "l" and width "w" to accommodate the final configuration of the flexible sheath 40. For example, the first and second layers may have a width 'w' of about 8 cm to accommodate a range of flexible endoscopic shafts 22. The length "l" is variable and in one embodiment may be about 100 cm. These dimensions are not limited and may be varied to accommodate any desired length "l" and width "w." A plurality of longitudinally extending structural members 56 are disposed between the first and the second sheaths 40 a, b and are separated by a distance "d." In one embodiment, the distance between the structural members 56 is about 13 mm. A bonding element 62 may be disposed in the spaces between the spaced apart structural members 56 such that the structural members 56 and the bonding elements 62 are alternately positioned along the width "w" of the first and second layers 40 a, b. The first and second layers 40 a, b with the structural members 56 and the bonding elements 62 disposed therebetween are bonded by the bonding elements 62 to form a unitary structure that can be rolled into a tubular shape to form the flexible sheath 40. As previously discussed, the flexible sheath 40 defines the opening 24 for receiving therein a suitably sized flexible endoscopic shaft 22. The flexible sheath 40 may have various thicknesses and in one embodiment may have a thickness of about 0.5 mm (e.g., about 20 mils). Although the various components of the flexible sheath 40 may have many configurations, in the illustrated embodiment, the first and second layers 40 a, b can be made of TYVEK® sheets and the structural members 56 can be made of NITINOL wire having a diameter of about 0.0335 mm, for example. In other embodiments, the reinforcing structural members 56 may be configured steel springs or polymeric columns. In one embodiment, a structural reinforcing structural member 56 may be configured as an external endorail longitudinally extending along an exterior surface of the flexible sheath 40. In one embodiment, the bonding elements 62 may be formed of two-part epoxy.

FIG. 6 is a distal end view of one embodiment of the flexible overtube 12. Referring to FIGS. 1-3 and 6, in the illustrated embodiment, the distal end 17b of the flexible overtube 12 comprises a generally cylindrical end cap 51 with the tapered surface 52 and an internal circumferential radial protruding wall 64 that is configured to engage an endoscopic end cap 66 suitable to fit over the distal end 18b of the flexible endoscopic shaft 22. The wall 64 is dimensioned to stop the distal end 18b flexible endoscopic shaft 22 with the endoscopic end cap 66 from protruding through the distal end 17b of the flexible overtube 12. Although the cylindrical end cap 51 can have a variety of configurations, in one embodiment the cylindrical end cap 51 may be formed of molded soft plastic material, for example.

FIG. 7A is a cross-sectional view of the endoscopic end cap 66 and FIG. 7B is a distal end view the endoscopic end cap 66. The endoscopic end cap 66 comprises a proximal end 68a and a distal end 68b. The proximal end 68a defines an opening 70 configured to slidably receive the distal end 18b of the flexible endoscopic shaft 22. The distal end 18b of the flexible endoscopic shaft 22 butts against and engages a circumferential radial projection 72 to prevent the distal end 18b of the flexible endoscopic shaft 22 from protruding through the endoscopic end cap 66. The distal end 68b defines an opening 76 for receiving therethrough the distal end 18b of the flexible endoscopic shaft 22 when the end cap 66 is removed therefrom. The distal end 68b comprises a circumferential portion 74 configured to engage the circumferential radial protruding wall 64 of the end cap 51 of the flexible overtube 12. Although the endoscopic end cap 66 can have a variety of configurations, in one embodiment the endoscopic end cap 66 may be formed of plastic, such as clear see-through polycarbonate material, for example.

Figure 8A:
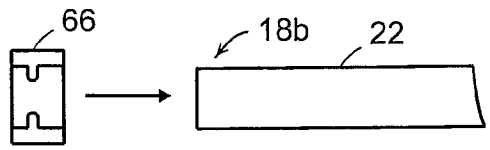
FIG. 8A illustrates one embodiment of the endoscopic end cap slidably inserted over the outside diameter of the distal end of the flexible endoscopic shaft.

A sequence of steps for using the flexible endoscopic translumenal overtube assembly 10 is illustrated in FIGS. 8A-F. Initially, the flexible overtube 12 is inserted into a natural orifice of the patient that is suitable to reach the tissue treatment region. As shown in FIG. 8A, the endoscopic end cap 66 is slidably inserted over the outside diameter of the distal end 18b of the flexible endoscopic shaft 22.

Figure 8B:
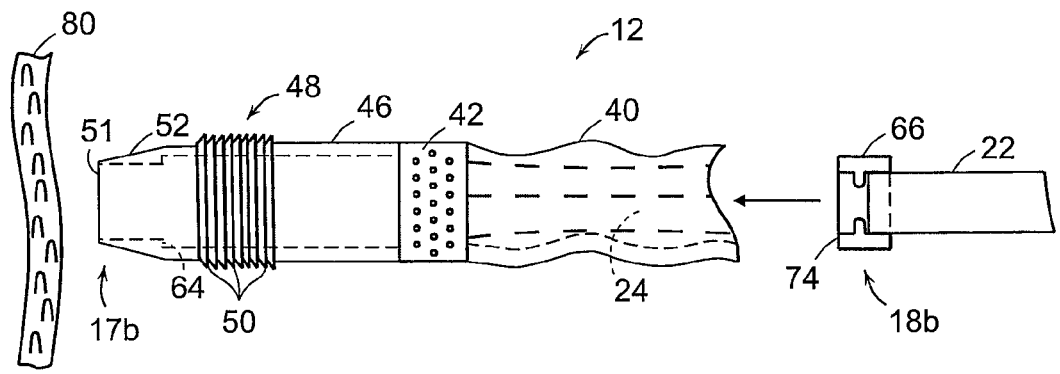
FIG. 8B illustrates the distal end of the flexible endoscopic shaft introduced into the distal end of one embodiment of the flexible overtube through the hollow lumen of the flexible overtube.

As shown in FIG. 8B, the distal end 18b of the flexible endoscopic shaft 22 is introduced into the distal end 17b of the flexible overtube 12 through the opening 24 of the flexible overtube 12. The flexible endoscopic shaft 22 is inserted into the cylindrical end cap 51 of the flexible overtube 12 until the circumferential portion 74 of the endoscopic end cap 66 engages the circumferential radial protruding wall 64 of the end cap 51 of the flexible overtube 12. The end caps 51, 66 fit together. The flexible endoscopic translumenal overtube assembly 10 is then located in proximity to a tissue wall 80.

Figure 8C:
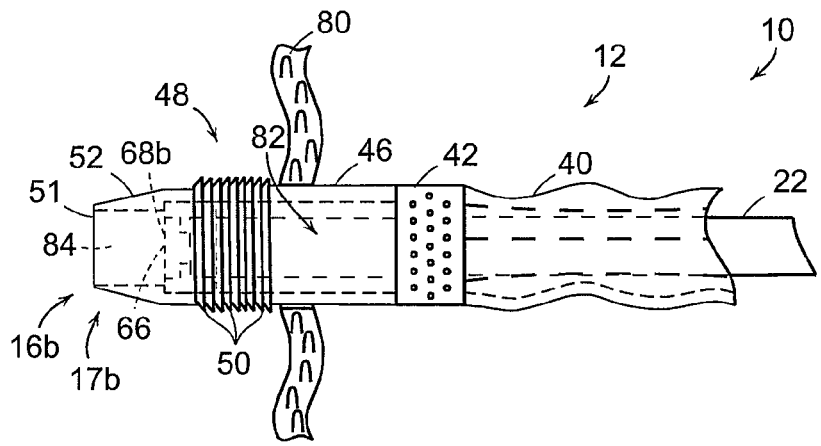
FIG. 8C shows one embodiment of a flexible endoscopic translumenal overtube assembly inserted through a dilated orifice formed in a tissue wall.

As shown in FIG. 8C, the distal tip 16b of the flexible endoscopic translumenal overtube assembly 10 is inserted through a dilated orifice 82 formed in the tissue wall 80. An example of how to puncture the tissue wall 80 and dilate the resulting orifice is discussed in more detail below. A space 84 is provided between the distal end 68b of the endoscopic end cap 66 and the distal end 17b of the flexible overtube 12. The space 84 is suitable to enable a dilation balloon to be inflated therein. Once the distal end 17b of the flexible overtube 12 is pushed through the dilated orifice 82 in the tissue wall 80, the tissue gripping stability feature 48 grips the tissue wall 80 to prevent the distal end 17b of the flexible overtube 12 from pulling away from the dilated opening 80.

Figure 8D:
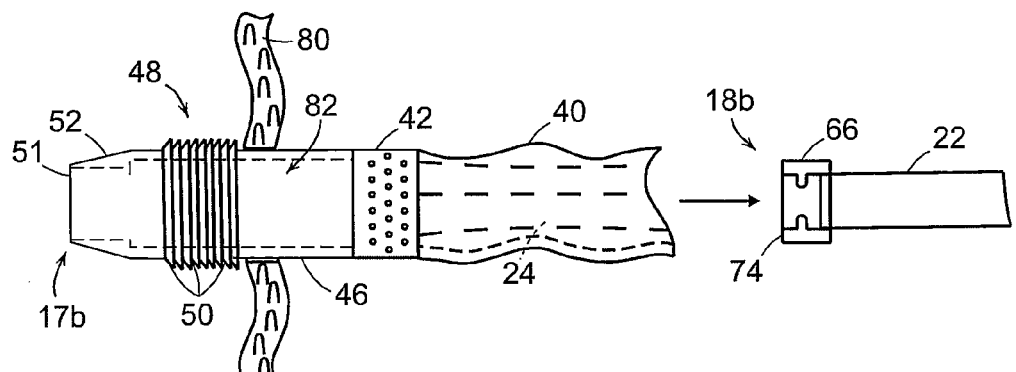
FIG. 8D shows one embodiment of a flexible endoscopic translumenal overtube assembly stabilized within a dilated orifice formed in a tissue wall.

As shown in FIG. 8D, the distal end 17b of the flexible overtube 12 is stabilized within the dilated orifice 82. The flexible overtube endoscopic shaft 22 end the endoscopic end cap 66 are then retracted from the cylindrical end cap 51 and are pulled out of the proximal end 17a (FIGS. 1, 2) of the flexible overtube 12b. Once the distal end 18b of the flexible endoscopic shaft 22 is removed from within the flexible overtube 12, the endoscopic end cap 66 is removed from the distal end 18b of the flexible endoscopic shaft 22.

Figure 8E:
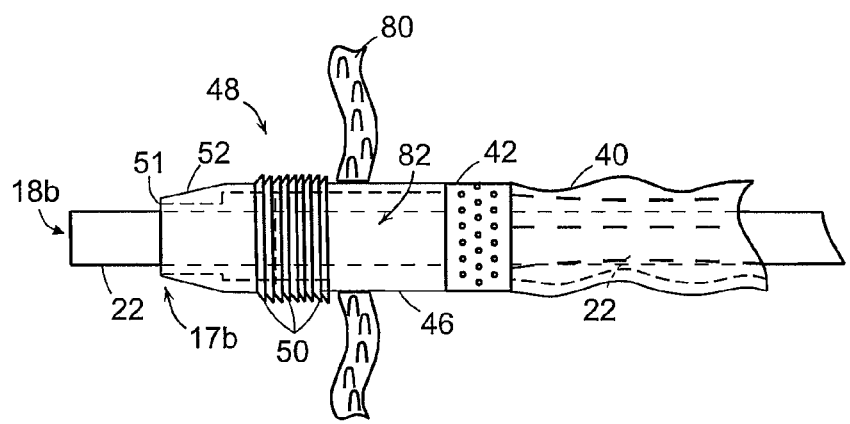
FIG. 8E shows a flexible endoscopic shaft reinserted into one embodiment of a flexible endoscopic translumenal overtube.

As shown in FIG. 8E, the flexible endoscopic shaft 22 is reinserted into the opening 24 of the flexible overtube 12. Without the endoscopic end cap 66 in place, the distal end 18b of the flexible endoscopic shaft 22 is pushed through the distal end 17b of the flexible overtube 12 through the tissue wall 80. The endoscope 14 (FIGS. 1 and 3) can now be employed to perform the intralumenal endoscopic surgical procedure at the surgical worksite.

Figure 8F:
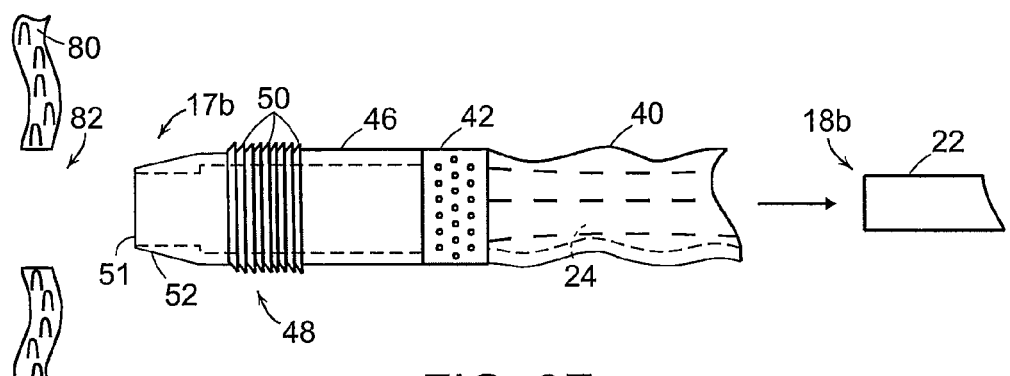
FIG. 8F shows one embodiment of a flexible endoscopic translumenal overtube assembly being removed from a dilated orifice formed in a tissue wall.

Once the procedure is concluded, as shown in FIG. 8F, the flexible endoscopic shaft 22 is retracted through the opening 24 of the flexible overtube 12. To remove the flexible overtube 12, the distal end 17b of the flexible overtube 12 is passed through the orifice 82. The dilation balloon is inflated to dilate the orifice 82 enough to overcome the tissue gripping effect of the stability feature 48. The flexible overtube 12 is then retracted through the dilated orifice 82 and pulled out of the patient through the natural opening of the patient.

Figure 9:
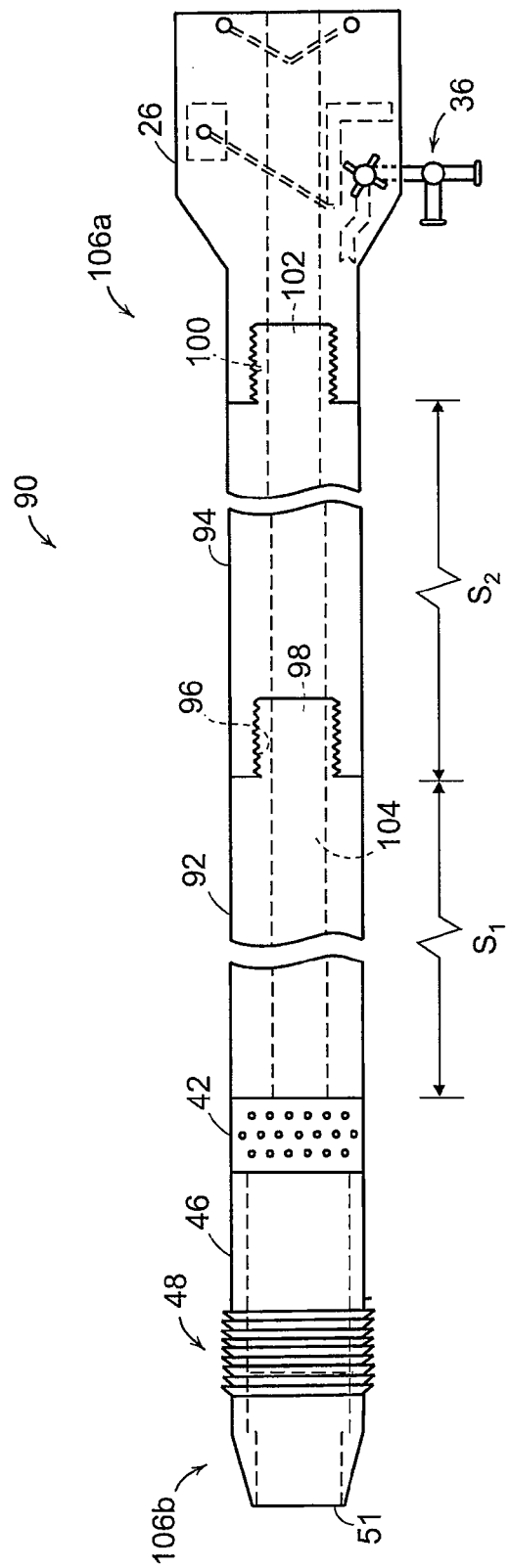
FIG. 9 illustrates one embodiment of a modular endoscopic overtube.

FIG. 9 illustrates one embodiment of a modular endoscopic overtube 90. The modular endoscopic overtube 90 may comprise adjustable segments at the proximal end 106a or the distal end 106b to adjust the length of the endoscopic overtube 90 or to add steerable segments at the distal end 106b. The overall length of a conventional endoscopic overtube is generally shorter than the overall length of the endoscope to enable the distal end of the flexible shaft of the endoscope to protrude though the distal end of the overtube to perform the endoscopic procedure. Longer endoscopic overtubes are easier to insert into the patient. Longer overtubes, however, interfere with the endoscopic procedure because they do not allow a sufficient length of the endoscopic flexible shaft to protrude into the body lumen or cavity (e.g., peritoneal cavity) to perform the endoscopic procedure at the worksite. The modular endoscopic overtube 90 may be employed with endoscopes having various different lengths and is easier to manufacture.

In one embodiment, the modular endoscopic overtube 90 comprises one or more modular segments such as a first removable segment 92 and a second removable segment 94. The first and second removable segments 92, 94 comprise central openings to form a central opening 104 to receive the flexible shaft of the endoscope. The distal first removable segment 92 may be a steerable segment or a straight substantially rigid segment. The removable segments 92, 94 may have variety of configurations. In one embodiment, each of the removable segments 92, 94 may have a length (e.g., $S_1$, $S_2$) from about 20 cm to about 30 cm.

The first removable segment 92 comprises a joining element 98 that is coupled to a corresponding joining element 96 of the second removable segment 94. The second removable segment 94 comprises another joining element 102 that may be coupled to another removable segment or, as shown in the illustrated embodiment, to a joining element 100 of the seal system 26. The joining elements 96, 98, 100, 102 may comprise barbs, quick connect features, or as shown in the illustrated embodiment, screw threads. The joining elements 96, 98, 100, 102 are low profile and provide a fluid tight seal and are able to be removed by the clinician during the procedure.

The removable segments 92, 94 may be removed or added before or during a procedure. Extending the length of the flexible overtube 90 by adding the removable segments 92, 94 before a procedure allows easier insertion of the flexile overtube 90 through a tissue wall inside the patient. Once the distal end 106 b of the flexible overtube 90 is inserted through the tissue wall and the endoscope is advanced into the body lumen or cavity, the flexible overtube 90 may be retracted and one or more of the removable segments 92, 94 may be removed to allow some extra room for the distal end of the flexible endoscopic shaft to perform the surgical procedure at the worksite.

Figure 10A:
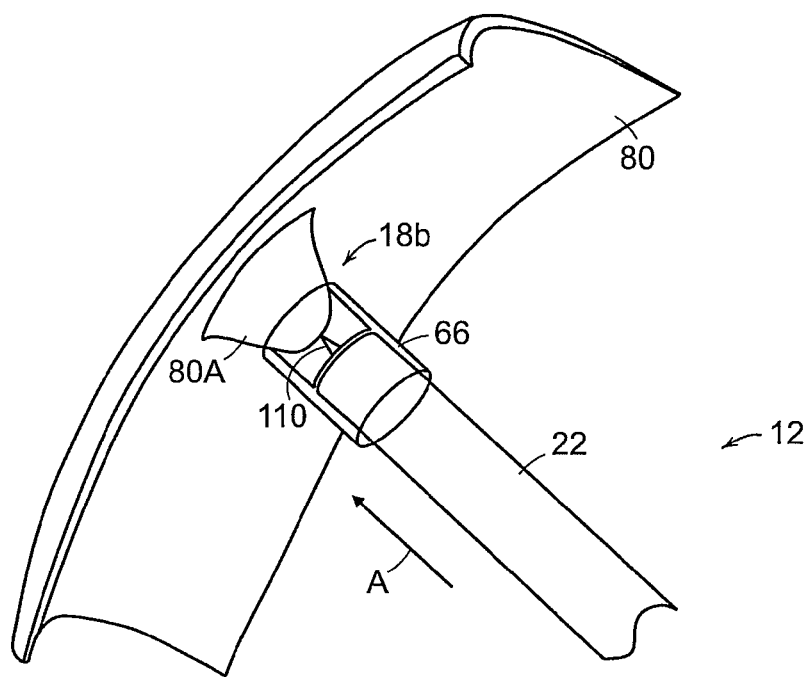
FIGS. 10A-N illustrate one embodiment of a method of introducing an endoscopic translumenal surgical device through the wall of a hollow organ during an endoscopic translumenal surgical procedure, where.
Figure 10B:
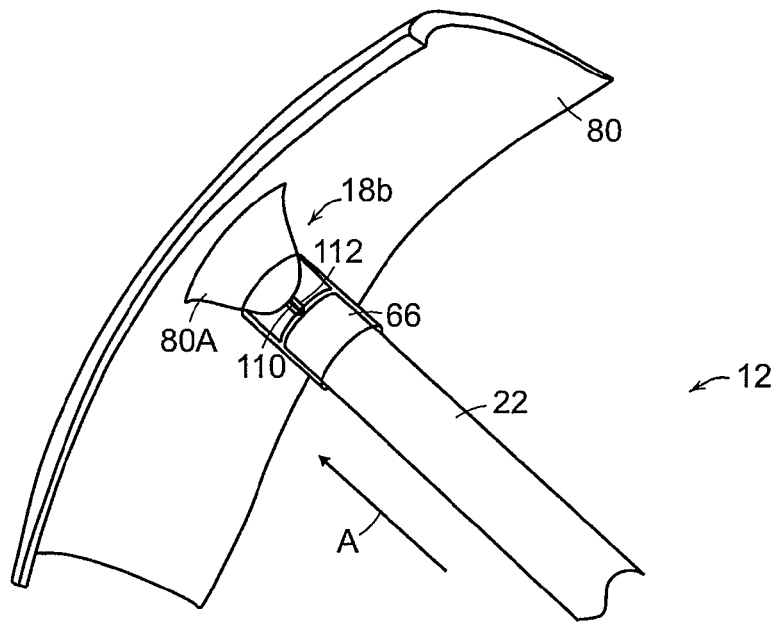
FIG. 10B illustrates an isolated tissue wall suctioned into one embodiment of an end cap and a flexible hollow tubular stylette advanced over a solid central needle.
Figure 10C:
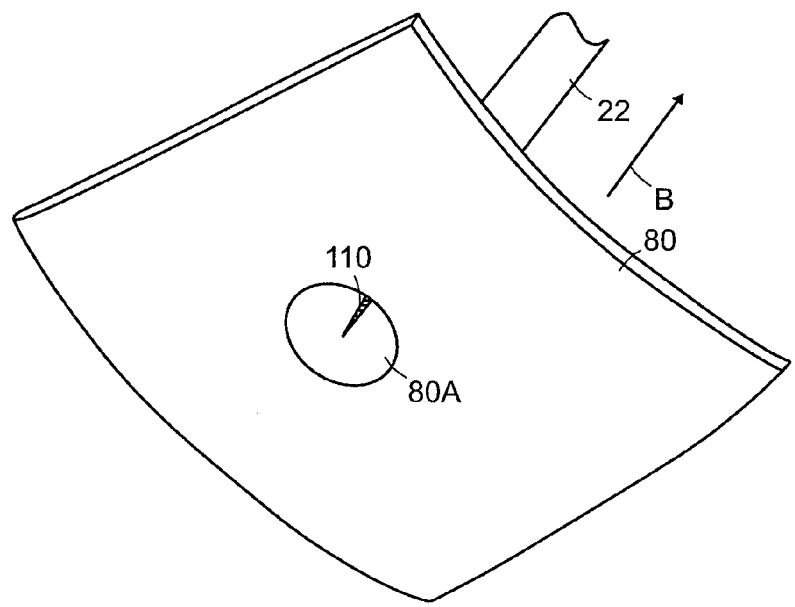
FIG. 10C illustrates one embodiment of a solid central needle advanced to pierce or puncture an isolated stomach wall tissue.
Figure 10D:
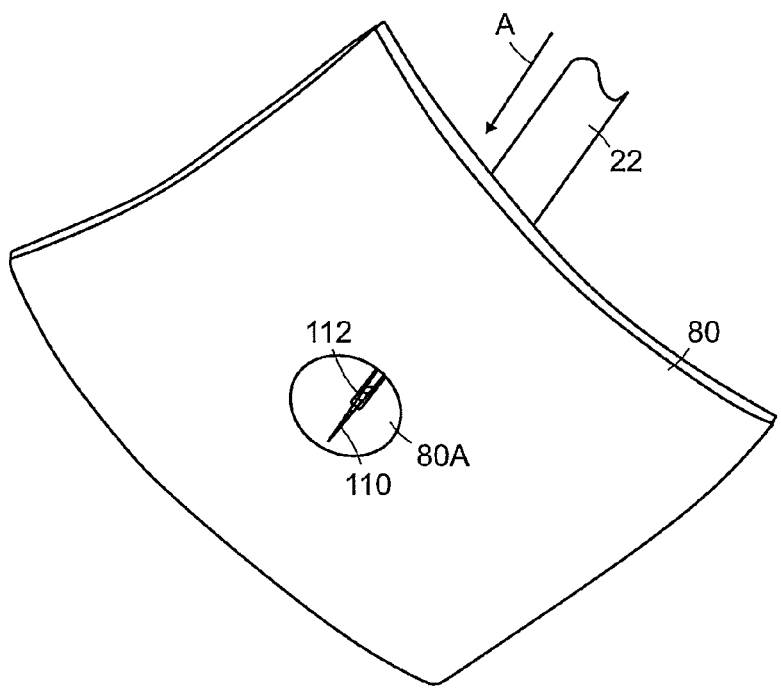
FIG. 10D illustrates one embodiment of the tubular stylette extended or advanced when the isolated stomach wall tissue is punctured with the solid central needle.
Figure 10E:
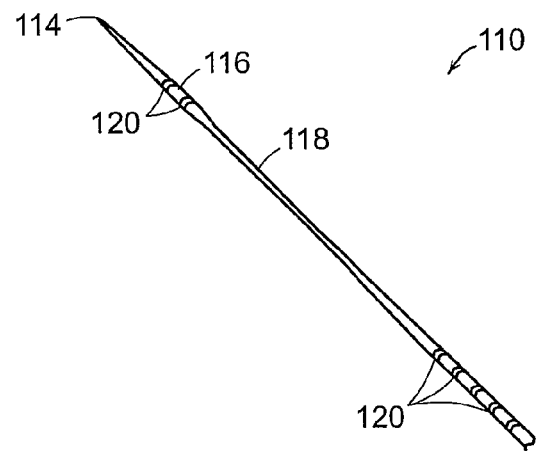
FIG. 10E illustrates one embodiment of a solid central needle comprising a sharp distal end and a dilating portion to pierce and spread the isolated stomach wall tissue to minimize cutting vessels and tissue.
Figure 10F:
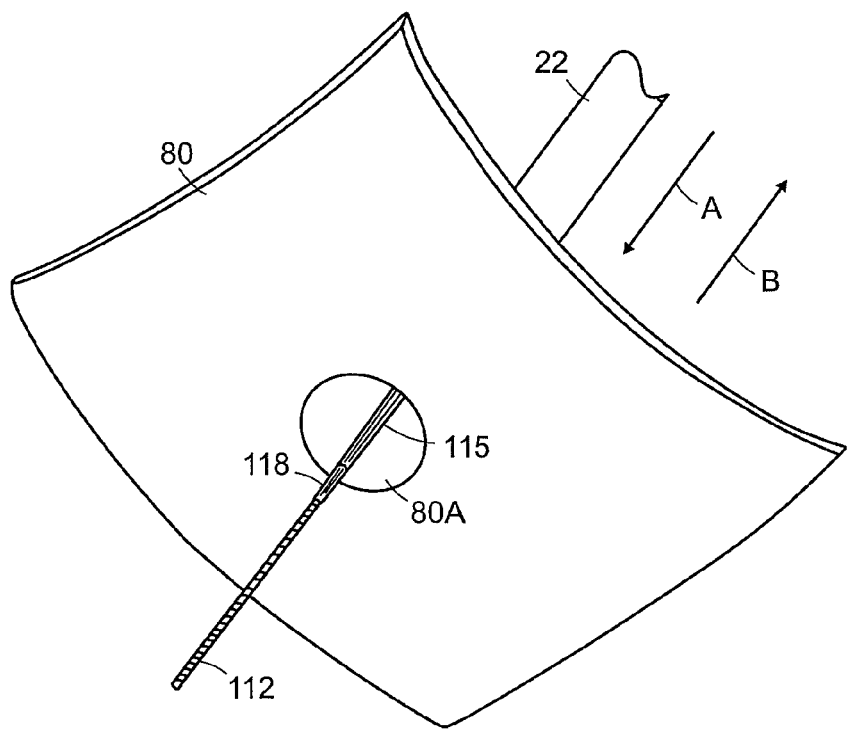
FIG. 10F illustrates one embodiment of a tubular stylette and a deflated balloon advanced through a puncture site of the isolated tissue, wherein the balloon is positioned simultaneously in the isolated stomach wall tissue and partially inside the distal end of the flexible overtube.
Figure 10G:
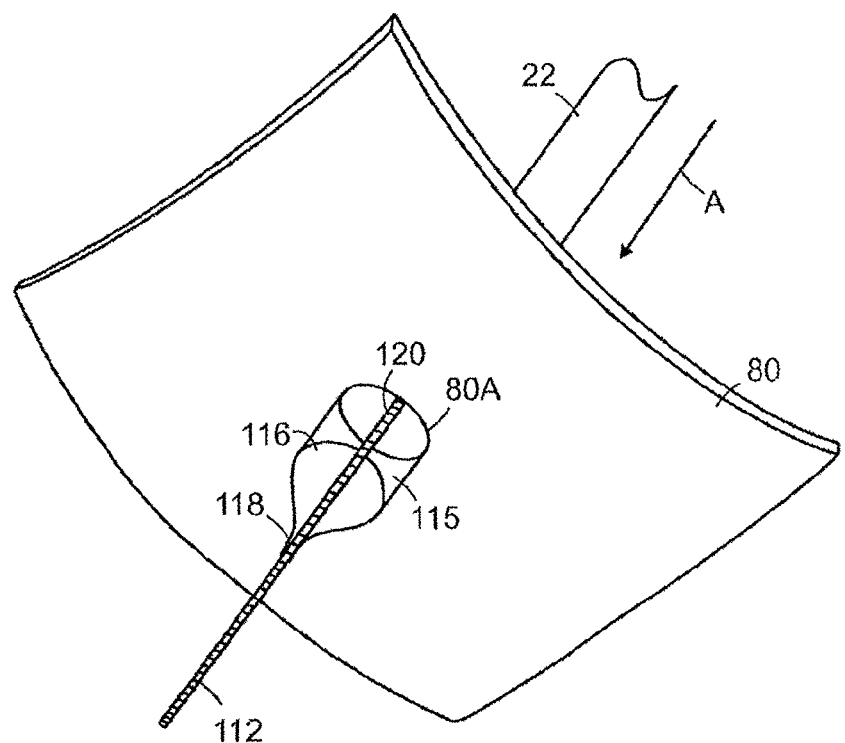
FIG. 10G illustrate one embodiment of an insufflated balloon to dilate the puncture in the isolated stomach wall tissue.
Figure 10H:
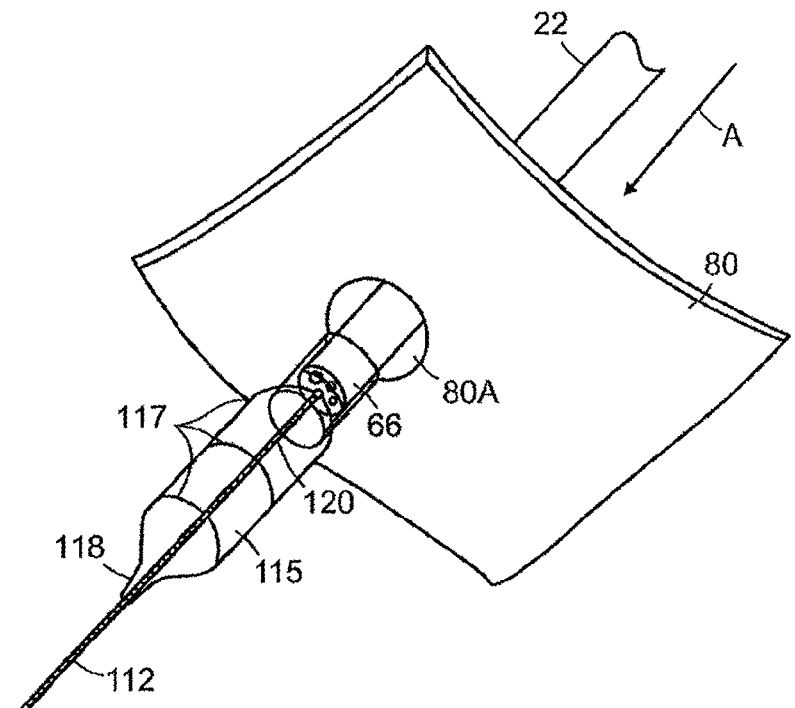
FIG. 10H illustrates one embodiment of a flexible endoscopic translumenal overtube assembly comprising a flexible overtube and an endoscope with an endoscopic end cap advanced through the dilated opening formed in the stomach wall tissue.
Figure 10I:
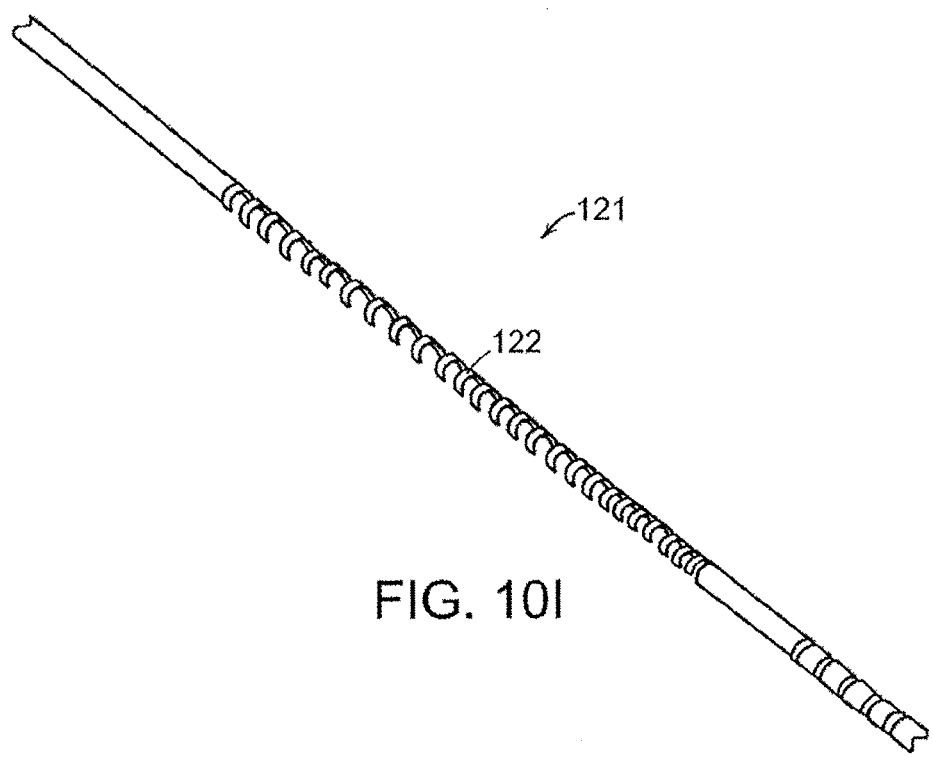
FIG. 10I illustrates one embodiment of a spring for biasing a tubular stylette introduced over a solid central needle.
Figure 10J:
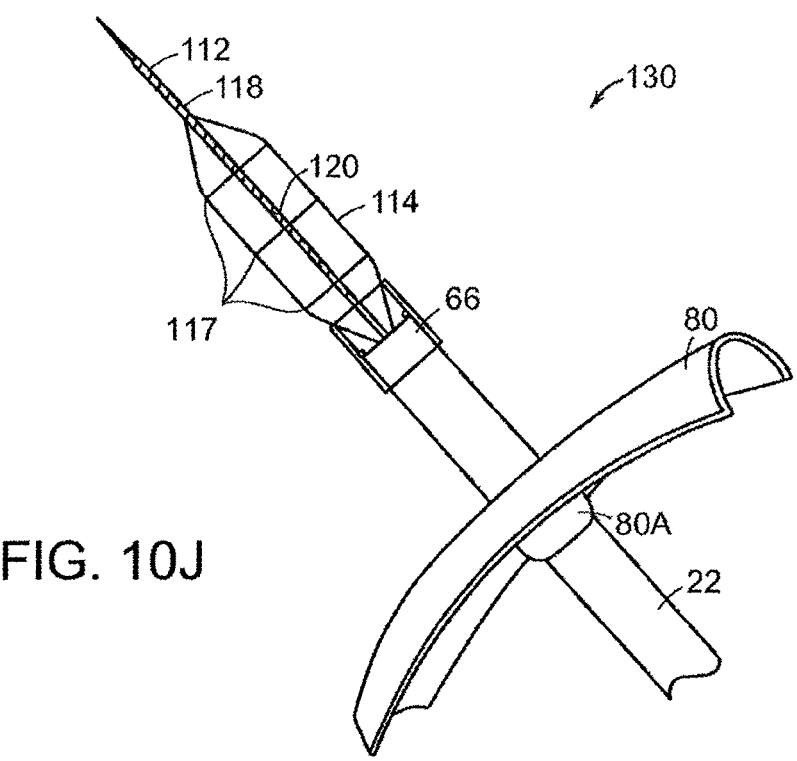
FIG. 10J shows one embodiment of an endoscopic translumenal surgical system.
Figure 10K:
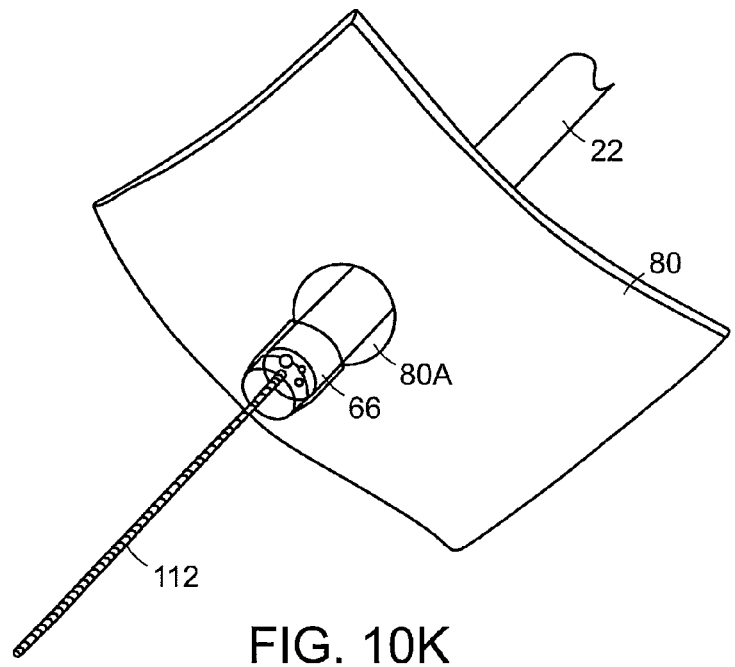
FIG. 10K shows one embodiment of a tubular stylette or solid central needle.
Figure 10L:
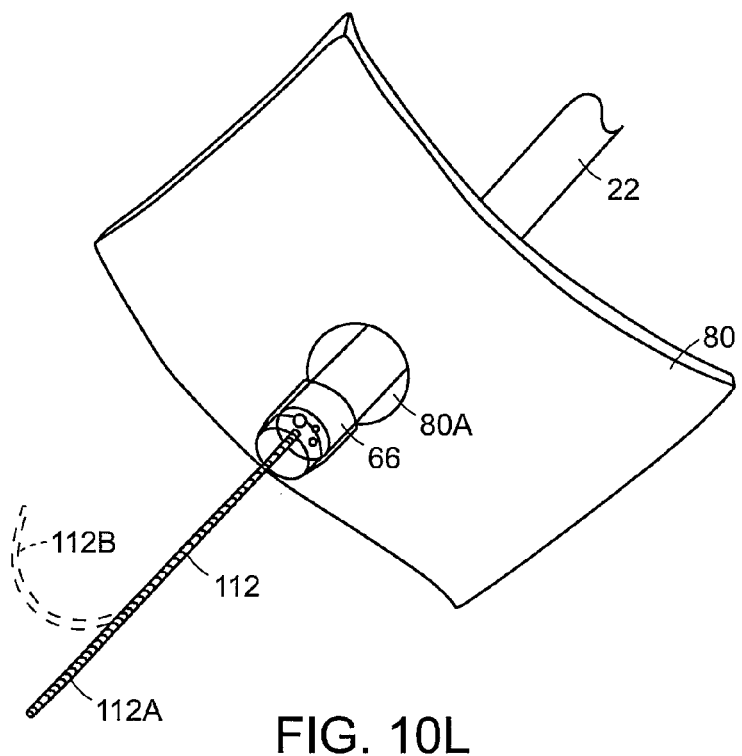
FIG. 10L shows one embodiment of a tubular stylette comprising a flexible feature.
Figure 10M:
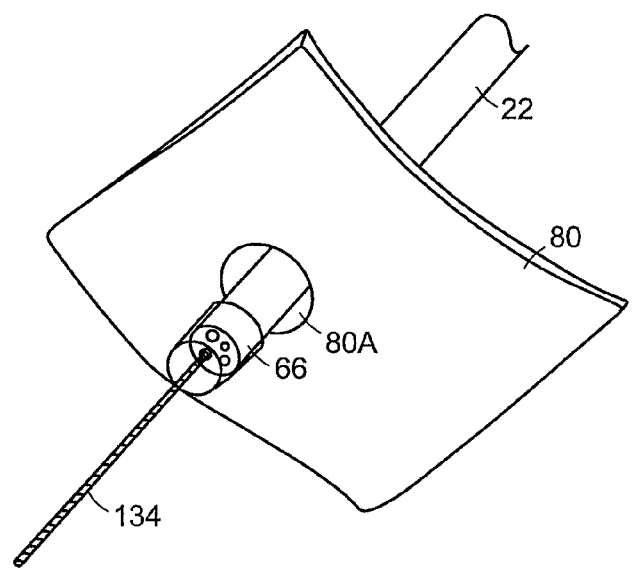
FIG. 10M shows one embodiment of a flexible central needle.
Figure 10N:
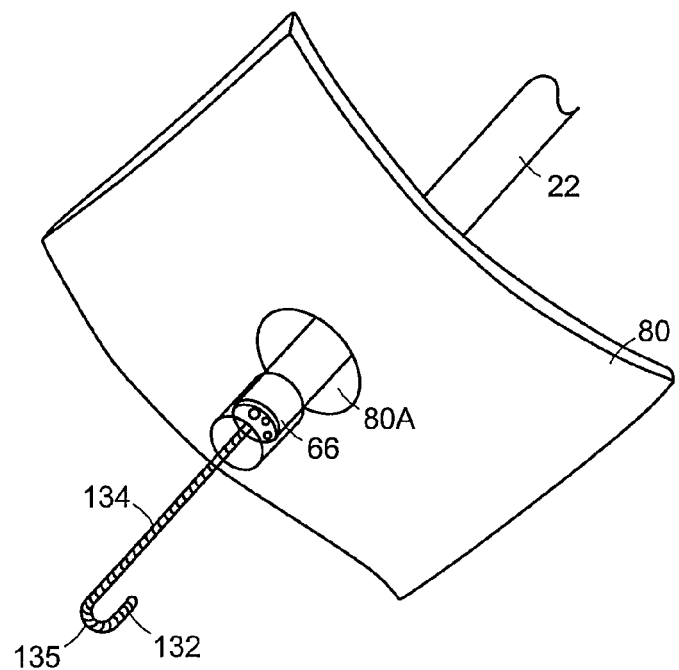

FIGS. 10A-N illustrate one embodiment of a method of introducing an endoscopic translumenal surgical device through the tissue wall of a hollow organ during an endoscopic translumenal surgical procedure. The endoscopic translumenal surgical devices should have certain attributes to minimize the severity of organ punctures when performing an endoscopic translumenal surgical procedure, especially during the initial access of the peritoneal cavity. It will be appreciated that the endoscopic translumenal surgical procedure illustrated with reference to FIGS. 10A-N may be performed using various embodiments of the flexible endoscopic translumenal overtube assembly 10 and/or the modular endoscopic overtube 90 described above. Accordingly, throughout the following description, reference also should be made to FIGS. 1-9 previously discussed.

In one embodiment of an endoscopic translumenal surgical procedure, the surgeon positions the endoscope 14 within the flexible overtube 12. The flexible endoscopic translumenal overtube assembly 10 comprising the flexible overtube 12 and the endoscope 14 are placed into a patient through a natural orifice, such as the esophagus to access the inside of a hollow organ such as the stomach. FIG. 10A, illustrates one embodiment of the flexible endoscopic shaft 22 of the endoscope inserted inside the stomach wall 80 and the distal end 18b of the endoscopic end cap 66 positioned in contact with the internal portion of the stomach wall 80. Negative pressure is applied to the endoscopic end cap 66 to isolate the portion of the tissue wall 80A to be pierced. To isolate the tissue wall 80A to be pierced, the clinician applies counter-traction. In the illustrated embodiment, this is achieved by applying suction at the distal end 18b of the flexible endoscopic shaft 22 through the endoscopic end cap 66. In other embodiments, the tissue wall 80A to be pierced may be isolated using a mechanical grabber such as a corkscrew or grasper, for example. In still other embodiments, the tissue wall 80A may be pierced without the aid of suction or other mechanical means. The endoscopic end cap 66 may have a variety of configurations. In the illustrated embodiment, the endoscopic end cap 66 is formed of a clear see-through material and enables tissue to be vacuumed or suctioned therein when a negative pressure is applied to the inside portion of the endoscopic end cap 66. The exterior surface of the endoscopic end cap 66 provides a smooth profile for tissue to glide over the entire flexible endoscopic translumenal overtube assembly 10. A solid central needle 110 is advanced in direction "A" until the solid central needle contacts the tissue wall 80A.

FIG. 10B illustrates the isolated tissue wall 80A suctioned into one embodiment of the end cap 66 and a flexible hollow tubular stylette 112 advanced over the solid central needle 110. The tubular stylette 112 may have a variety of configurations. In the illustrated embodiment, the tubular stylette 112 may be a hollow striped stylette, which slides with an internal balloon port over a striped tubular hollow stylette guidewire. In one embodiment, the tubular stylette 112 has a chamfered end. The solid central needle 110 may have a variety of configurations. In the embodiment shown in FIG. 10E, one embodiment of the solid central needle 110 comprises a sharp distal end 114 and a dilating portion 116 to pierce and spread the isolated tissue wall 80A and to minimize cutting vessels and tissue. The sharp distal end 114 and the dilating portion 116 contribute to self healing the pierced tissue wall 80A rather than bleeding out. A neck portion 118 behind the sharp distal end 114 and the dilating portion 116 enables tissue penetration only when the solid central needle 110 is sufficiently supported and guided within the tubular stylette 112. In one embodiment, the column strength of the solid central needle 110 may be reduced near the neck portion 118. Thus, if the solid central needle 110 protrudes too far outside of the tubular stylette 112, there will not be sufficient column strength to effect piercing. If the solid central needle 110 advances too far out in front of the tubular stylette 112 and a piercing force is applied to the solid central needle 110, the solid central needle 110 will bend before it pierces the tissue wall 80A. A plurality of stripes 120 are formed on the body of the solid central needle 110 to assist the clinician gage and monitor the movement and the extent of placement of the solid central needle 110 into the target tissue wall 80A site. In one embodiment, the solid central needle 110 may be an ultrasharp hollow ground needle, for example. The solid central needle 110 provides control of needle insertion speed into the isolated tissue wall 80A to be pierced because of the low insertion force of the sharp distal end 114 and the small diameter of the necked portion 118 of the solid central needle 110. This configuration requires minimal insertion force and does not create excessive potential energy storage that could cause a sudden insertion surge. Rather, the configuration provides a gradual and smooth advancement of the solid central needle 110 into the isolated tissue wall 80A to be pierced. The stripes 120 provide a visual indicator as feedback and verification to the clinician that the intended tissue wall 80A has been breached. The stripes 120 also provide feedback as to the depth of penetration of the solid central needle 110. The stripes 120 may be formed on the solid central needle 110 and/or on the tubular stylette 112. In one embodiment, this also may be achieved by providing detents on the instrument handle. In other embodiments, a tactile feedback mechanism may be provided such as a click or sudden resistance change, for example. In other embodiments, feedback may be provided by direct intramural vision during insertion using an optiview style cannula over the solid central needle 110, for example.

FIG. 10C illustrates one embodiment of the solid central needle 110 advanced to pierce or puncture the isolated stomach tissue wall 80A. It will be appreciated by those skilled in the art that the isolated stomach tissue wall 80A can be punctured without using electrocautery. The solid central needle 110 punctures the tissue wall 80A suctioned or vacuumed against the endoscopic end cap 66. Once the isolated tissue 80A is punctured, the solid central needle may be retracted in direction "B" and the tubular stylette 112 may be extended or advanced in direction A, as shown in FIG. 10D.

FIG. 10F illustrates one embodiment of the tubular stylette 112 and a deflated balloon 115 advanced through the puncture site of the isolated tissue wall 80A. The balloon 115 is positioned simultaneously in the isolated tissue wall 80A and partially inside the distal end of the flexible overtube 12 (not shown in FIG. 10F). The deflated balloon 115 is positioned behind a tapered dilating tip 118, which is ideally made of a clear see-through material. The balloon 115 is deflated when it is extended in direction A through the tissue wall 80A. The tubular stylette 112 and/or the solid central needle 110 may be left in place or may be retracted in direction B as may be needed during the procedure. In one embodiment, the balloon 115 may be formed of a clear see-through material and contain a pattern of stripes on its surface that indicate the ends of the balloon 115 and its center. For example, one thin stripe on the proximal end of the balloon 115, one thick stripe in its center, and one think stripe on the distal end of the balloon 115. Likewise, other stripe patterns may be employed.

FIG. 10G illustrates one embodiment of the balloon 115 when it is inflated to dilate the orifice formed in the tissue wall 80A at the puncture site. Enlarging or dilating the tissue wall 80A at the puncture site allows the flexible endoscopic shaft 22 to pass through the dilated opening.

FIG. 10H illustrates one embodiment of the flexible endoscopic translumenal overtube assembly 10 comprising the flexible overtube 12 and the endoscope 14 comprising the endoscopic end cap 66 advanced through the dilated opening in the tissue wall 80 A. The flexible overtube 12, the endoscope 14, and the endoscopic end cap 66 are advanced after the isolated tissue wall 80 A is dilated. The inflated balloon 115 exposes positioning stripes 117 to assist the clinician in placing and guiding the flexible endoscopic translumenal overtube assembly 10 through the hollow organ tissue wall 80.

As shown in FIGS. 10G, H, and I, a spring 121 may be employed to bias the tubular stylette 112 introduced over the solid central needle 110. The spring 121 may comprise a spiral kerf 122 to provide a physical shield to shroud the sharp solid central needle 110 in order to protect underlying organs from inadvertent puncture and is perceivable by the clinician. The configuration wherein the spring 121 is used to shroud the sharp solid central needle 110 may be referred to as a veress needle configuration. Those skilled in the art will appreciate that a veress needle is a needle equipped with a spring loaded obturator that is used for insufflation of the abdomen in laparoscopic or endoscopic surgeries. In other embodiments, means may be provided to automatically terminate the piercing function after the isolated tissue wall 80A has been pierced or breached.

FIG. 10J is an overall view of the endoscopic translumenal surgical system 130 described above.

As shown in FIG. 10K, the balloon 115 has been deflated and withdrawn. This leaves the tubular stylette 112 and/or the solid central needle 110 behind to be used as a guidewire.

As shown in FIG. 10L, the tubular stylette 112 has a flexible feature and can be articulated from a straight position 112A to a flexed position 112B, shown in broken line, by the clinician.

FIG. 10M illustrates one embodiment of a flexible central needle 134. In the illustrated embodiment, the flexible central needle 134 is formed with a smaller neck portion at the distal end to allow the solid central needle 134 to flex. When pulled mostly inside the balloon 115 catheter and the tubular stylette 112, the column strength of the solid central needle 110 is very strong, and therefore will puncture the tissue wall 80 suitably well.

As shown in FIG. 10N, the flexible central needle 134 is fully extended (unsupported) and is shown in the flexed state with a flexed portion 132. In the flexed state, the flexible central needle 134 presents a blunt distal 135 end and will not puncture tissue. Thus, the flexible central needle 134 can be flexed and used as guidewire, for example. In one embodiment, the flexible central needle 134 may be drawn inside the tubular stylette 112 and housed therein during use as a guidewire.

Figure 11A:
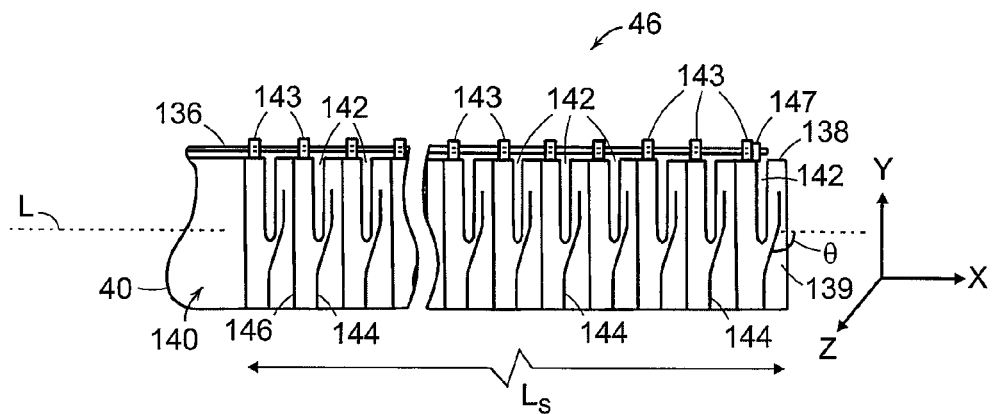
FIG. 11A is a side view of one embodiment of a steerable segment of one embodiment of the flexible overtube shown in FIGS. 1 and 2.
Figure 11B:
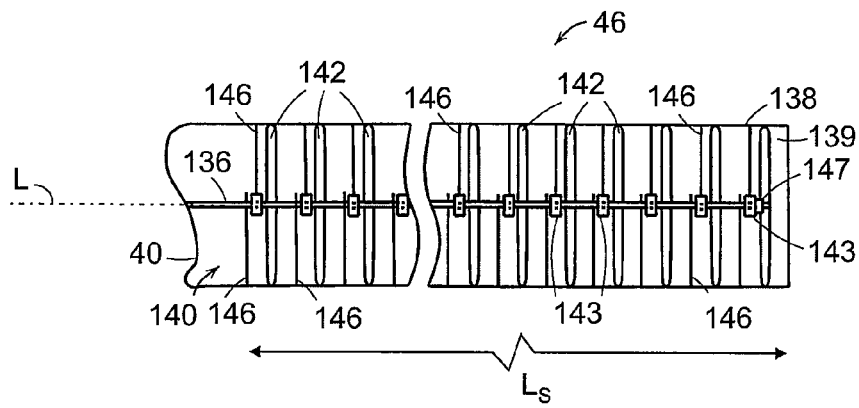
FIG. 11B is a top view of one embodiment of the steerable segment shown in FIG. 11A.
Figure 11C:
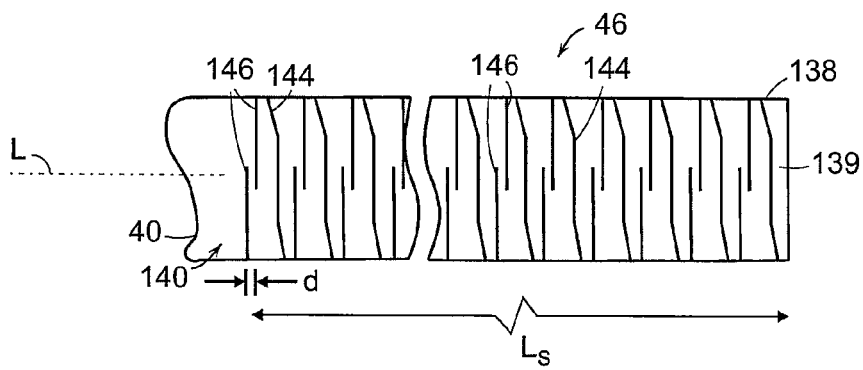
FIG. 11C is a bottom view of one embodiment of the steerable segment shown in FIG. 11A.
Figure 12:
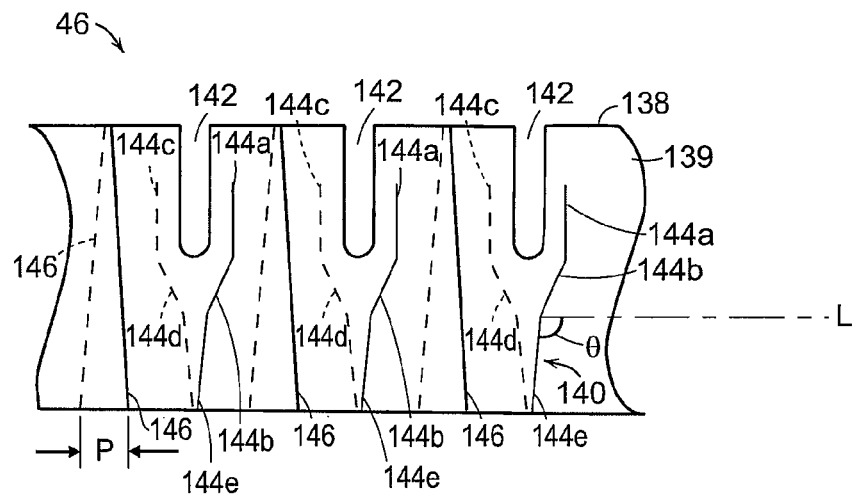
FIG. 12 is a side view of one embodiment of the steerable segment shown in FIGS. 11A-C.
Figure 13:
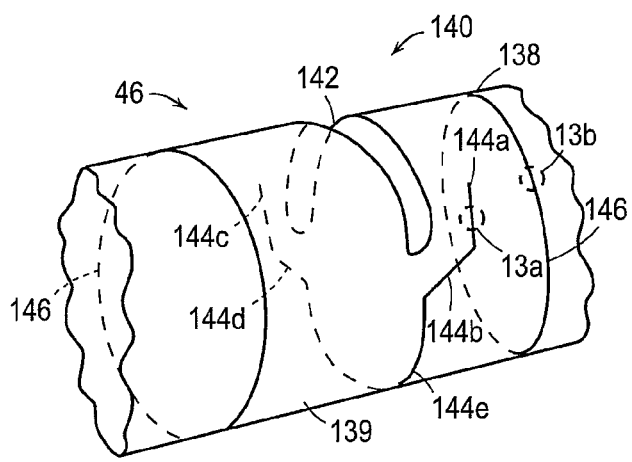
FIG. 13 is a perspective view of a portion of the steerable segment shown in FIGS. 11A-C and 12.
Figure 13B:
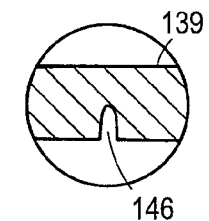
FIG. 13B is a cross-sectional view of a wall portion of the steerable segment shown in FIG. 13.
Figure 13A:
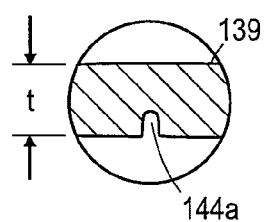
FIG. 13A is a cross-sectional view of a wall portion of the steerable segment shown in FIG. 13.

FIGS. 11A-C illustrate one embodiment of an actively articulatable steerable tube 138 portion of the steerable segment 46. The steerable tube 138 is shown without a protective layer that is slidably received over the steerable tube 138 to form a fluid tight seal. FIG. 12 is a side view of one embodiment of the steerable segment shown in FIGS. 11A-C. FIG. 13 is a perspective view of a portion of the steerable segment shown in FIGS. 11A-C and 12. FIG. 13A is a cross-sectional view of a wall portion of the steerable segment shown in FIG. 13. FIG. 13B is a cross-sectional view of a wall portion of the steerable segment shown in FIG. 13.

In the embodiment illustrated in FIGS. 11A-C, the steerable tube 138 comprises a series of slits 140 cut into the body 139 defining a pattern of articulatable elements to enable active articulation of the steerable tube 138 in a first plane XY and passive deflection in planes XZ and YZ that are orthogonal to the first plane. The slits 140 may be cut into the steerable tube 138 in a variety of patterns to assist with flexure in the direction of the pull cable 136 plane (XY in the embodiment illustrated in FIG. 11A). In one embodiment, the steerable segment 46 and/or the steerable tube 138 has a length $L_S$ of about 20 cm.

In one embodiment, the steerable tube 138 comprises a pattern of slits 140 cut in a pattern on the body 139. In one embodiment, the pattern of slits 140 comprises a series of apertures 142, S-shaped slits 144, and spiral slits 146 formed along the longitudinal length of the body 139 of the steerable tube 138. As shown in FIGS. 11A-C, the pattern of slits 140 is repeated along the longitudinal axis L. In one embodiment, the apertures 142 are about 1 mm wide and spaced apart by about 4 mm. The S-shaped slits 144 begin on one side of the body 139 of the steerable tube 138 and wrap around to the other side. The S-shaped slits 144 comprise a first portion 144a that is perpendicular to the longitudinal axis "L" of bending. The first portion 144a has a length of about 6 mm. A second portion 144b forms an angle θ between about 100 to about 110 degrees with the longitudinal axis "L" and has a length of about 6 mm (FIGS. 11A and 12). A third portion 144c is parallel to the first portion 144a and has a length of about 10 mm. A fourth portion 144d is parallel to the second portion 144b and has a length of about 6 mm. A fifth portion 144e is parallel to the first portion 144a and the third portion 144c and has a length of about 6 mm. The spiral slits 146 are in the form of a helix and make one revolution around the body 139 of the steerable tube 138 with an overlap "d" (FIG. 11C) of about 1.5 mm and a pitch "p" of about 1.25 mm. In the illustrated embodiment, the spiral slits 146 are positioned between the apertures 142 and the S-shaped slits 144. In other embodiments, the apertures 142, S-shaped slits 144, and spiral slits 146 may be positioned relative to each other in any predetermined arrangement.

The steerable tube 138 is attached to at least one of the pull cables 136 such that it can be actively articulated in the XY plane away from the neutral longitudinal axis "L." In one embodiment, in the active articulation direction, e.g., the XY plane, the steerable tube 138 can be articulated through angles up to about 180 degrees when tension is applied to the pull cable 136 and can passively flex about 45 degrees in the directions orthogonal to the active articulation direction. In another embodiment, the steerable tube 138 can be passively articulated in the XZ plane orthogonal to the XY plane defined by the pull cable 136 through angles up to about 90 degrees. The pull cable 136 may be loosely threaded through a series of rings 143 disposed along an outer portion of the hollow body 139 along the longitudinal length of the steerable tube 138 and is fixedly attached to at least one of the rings 143 such that the steerable tube 138 bends when tension is applied to the pull cable 136. In the illustrated embodiment, the distal end of the pull cable 136 is fixedly attached to the ring 143 located at the distal end of the steerable tube 138 by a crimp, lock, or knot feature 147 to prevent the pull cable 136 from being pulled through the distal ring 143. Thus, when tension is applied to the pull cable 136, the flexible tube 138 bends or articulates in the XY plane defined by the pull cable 136.

To assist straightening of the steerable segment 46, the body 139 of the steerable tube 138 may be constructed of full-hardened steel that tends to spring back more readily than softened annealed metal. In another embodiment, a straightening member may be disposed along the longitudinal axis "L" to provide a spring force that tends to straighten the steerable segment 46 when tension in the pull cable 136 is released. The straightening member may be made from a superelastic alloy such as NITINOL® wire, spring steel, music wire, or other material having a suitable level of elastic deformation and stored energy to straighten the steerable segment 46. In one embodiment, the straightening member may be positioned adjacent to the pull cable 136 and may be allowed to freely float on its proximal end. In another embodiment, the straightening member may be positioned orthogonal to the pull cable 136 and periodically fixed to the surface of the steerable tube 138 through welds or other connection means.

Referring now to FIGS. 1, 2, 4, and 11-13B, in one embodiment, the steerable segment 46 may comprise the steerable tube 138 shown in FIGS. 11A-C, 12, 13A, 13B (FIGS. 11-13B). As shown in FIGS. 1 and 2, the steerable segment 46 is located at the distal end 17b of the flexible overtube 40. The steerable tube 138 comprises an elongate hollow body 139 defining a central opening suitable for receiving an endoscope therein. A series of slits 140 are formed into the body 139 defining a plurality of articulatable elements to make the steerable tube 138 flexible while still providing sufficient column strength to advance the steerable tube 138 through a passageway leading to a body cavity within the patient. In one embodiment, the inside diameter of the steerable tube 138 may be selected to enable an endoscope to freely slidably move within the steerable tube 138 when it is articulated. For example, the inside diameter of the steerable tube 138 may be about 10 mm for a single channel diagnostic endoscope and about 15 mm for a two-channel endoscope.

The steerable tube 138 may be formed of a variety of materials including metallic materials, steel, brass, polycarbonate, polyetheretherketone (PEEK), urethane, or polyvinylchloride (PVC). In one embodiment, the steerable tube 138 may be constructed of full-hardened steel that tends to spring back more readily than softened annealed metal. The wall thickness "t" of the body 139 of the steerable tube 138 may range from about 0.25 mm to about 1 mm.

In one embodiment, the series of slits 140 may be formed with a laser cutter. In other embodiments, the series of slits 140 may be formed with a machine bit or other suitable means for forming a substantially narrow cut, opening, or aperture, for example. In one embodiment, the series of slits 140 may be cut into the body 139 in a predetermined pattern without removing sections or portions of the material other than the kerf. As shown in FIGS. 13A and 13B portions of the series of slits 140, such as the S-shaped slits 144 and the spiral slits 146, for example, may be formed on an outer surface portion of the body 139 without entirely penetrating the wall thickness "t" of the body 139. In another embodiment, the series of slits 140 may be formed by removing sections or portions of the material along its length. In yet another embodiment, the series of slits 140 may be formed by creating a mold of a desired form and shape and then molding the steerable tube 138 using conventional plastic molding techniques. It will be appreciated that any combination of these techniques may be employed to form the series of slits 140 in a predetermined pattern defining a plurality of articulatable elements that render the steerable tube 138 flexible yet sufficiently rigid to provide adequate column strength for insertion through a passageway leading to a body cavity within the patient. The embodiments are not limited in this context.

Figure 14:
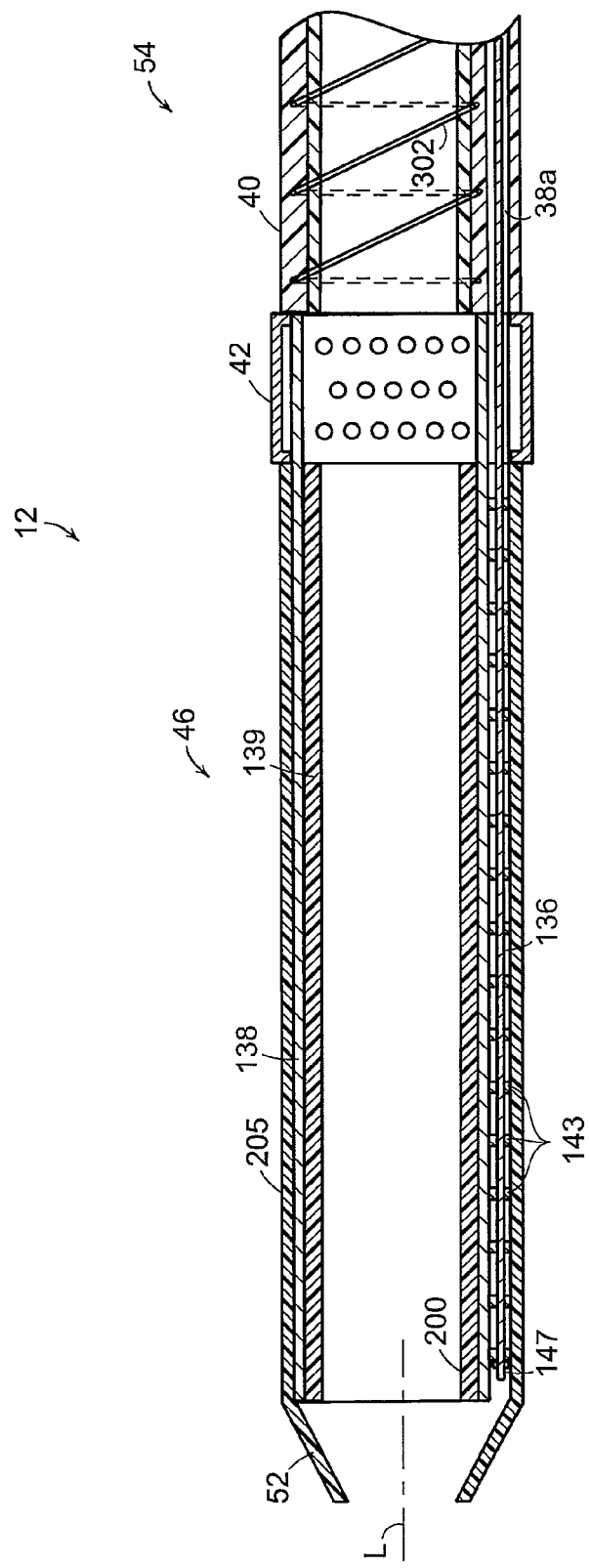
FIG. 14 is a cross-sectional view of the steerable segment and a middle segment of the flexible overtube shown in FIGS. 1 and 2.

FIG. 14 is a cross-sectional view of the steerable segment 46 and the middle segment 54 of the flexible overtube shown 12 shown in FIGS. 1 and 2. In one embodiment, the steerable segment 46 may comprise the steerable tube 138, previously described with reference to FIGS. 11-13B, comprising a first layer of flexible material disposed on an inner portion of the steerable tube 138 and a second layer of flexible material disposed on an outer portion of the steerable tube 138 to maintain a fluid tight seal. In one embodiment, the steerable segment 46 comprises an inner woven boot 200, an outer flexible boot 205, and the steerable tube 138 coaxially floating between the inner woven boot 200 and the outer flexible boot 205. The inner woven boot 200, the outer flexible boot 205, and the steerable tube 138 are connected at their proximal and distal ends. The inner woven boot 200 can be constructed of polypropylene, or polyethylene strands woven into a tube having an inner diameter of about 15.5 mm. The outer flexible boot 205 may be extruded or molded from one continuous piece. In one embodiment, the tapered segment 52 and stability threads (not shown in FIG. 14 for clarity) may be formed integrally with the molded outer flexible boot 205 component. The outer flexible boot 205 is placed over the steerable tube 138 and is fixed at the distal and proximal ends through heat forming, epoxy or other adhesives. Suitable materials for the outer flexible boot 205 include polyurethane, isoprene, fluoroelastomer (VITON®), silicone, or other flexible materials. In one embodiment, the middle segment 54 comprises a flexible polymeric tube, e.g., the flexible sheath 40, reinforced by an embedded spring 302. The spring 302 has a wire diameter of about 0.310 mm and the outer coil diameter of the spring 302 may range from about 7 mm to about 17 mm. The spring 302 may be sandwiched between two layers of polymer, such as polyurethane, silicone, polymers (PEBAX®), or other suitable material. The outer diameter of the middle segment 54 may range from about 8 mm to about 18 mm.

Figure 15:
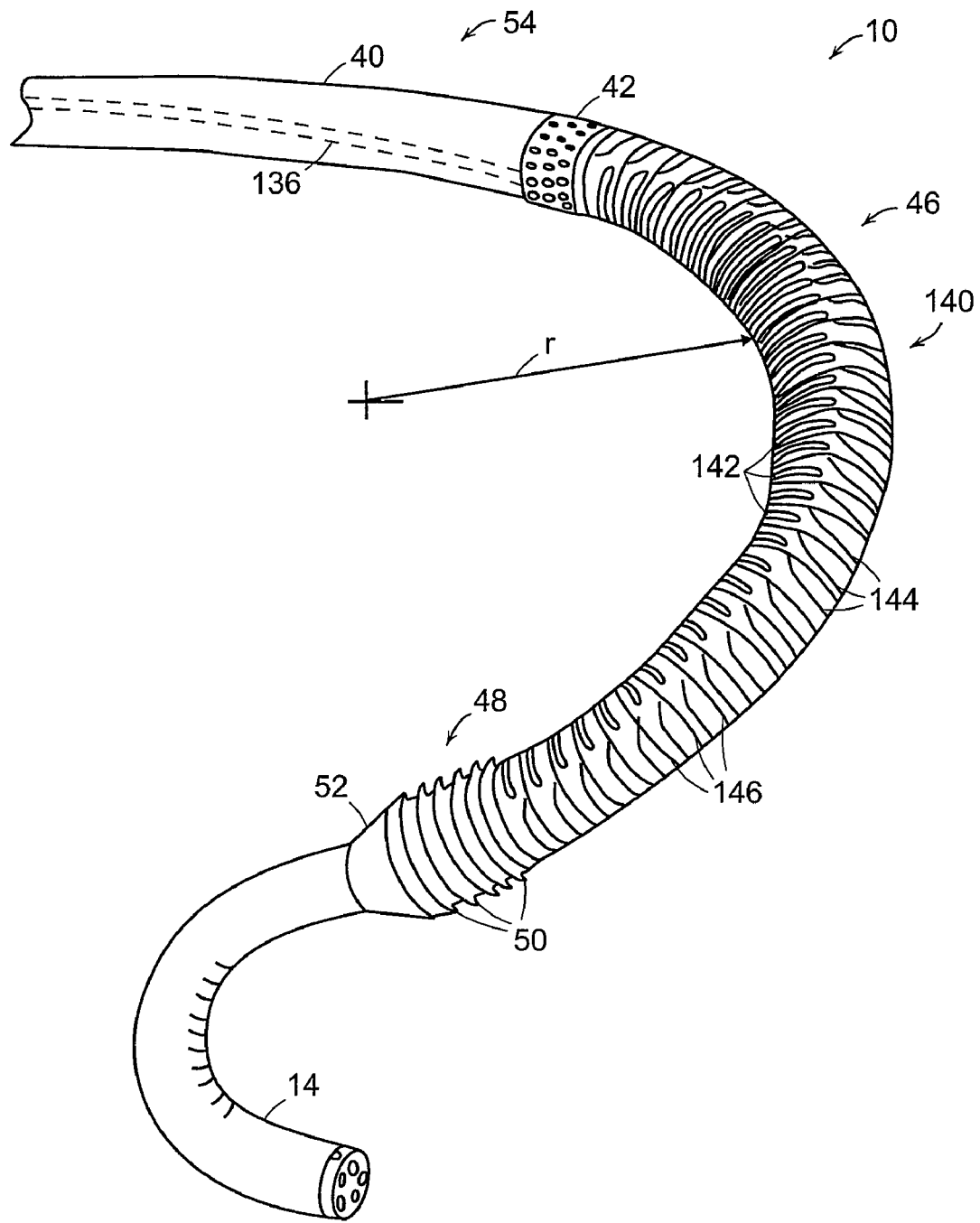
FIG. 15 illustrates a steerable segment of the flexible endoscopic translumenal overtube assembly shown in FIG. 1 in an actuated state.

FIG. 15 illustrates the steerable segment 46 of the flexible endoscopic translumenal overtube assembly 10 shown in FIG. 1 in an actuated state. With reference now to FIGS. 1, 2, and 11-15, the pull cable 136 extends from a distal portion of steerable segment 46, through the first lumen 38a, and extends out of the proximal end of the flexible sheath 40. As previously discussed, the distal end of the pull cable 136 is fixedly attached to the distal end of the steerable tube 138 by a crimp, lock, or knot feature 147 to prevent the pull cable 136 from being pulled through a distal ring 143. Thus, when tension is applied to the pull cable 136 by the actuation handle 300, the steerable segment 46 bends in the XY plane away from its neutral axis in a radius of curvature "r" through angles up to about 180 degrees as may be defined by the pattern or series of slits 140 in the active articulation direction and about 45 degrees of passive flexion in the directions orthogonal to the active direction. A desired radius of curvature "r" allows the endoscope 14 to be inserted and withdrawn without the need to straighten the steerable segment 46. A suitable bend radius is between about 3 cm to about 5 cm. The portion extending beyond the flexible sheath 40 is contained in the coil pipe assembly 210 that extends to the actuation handle 300.

Figure 16:
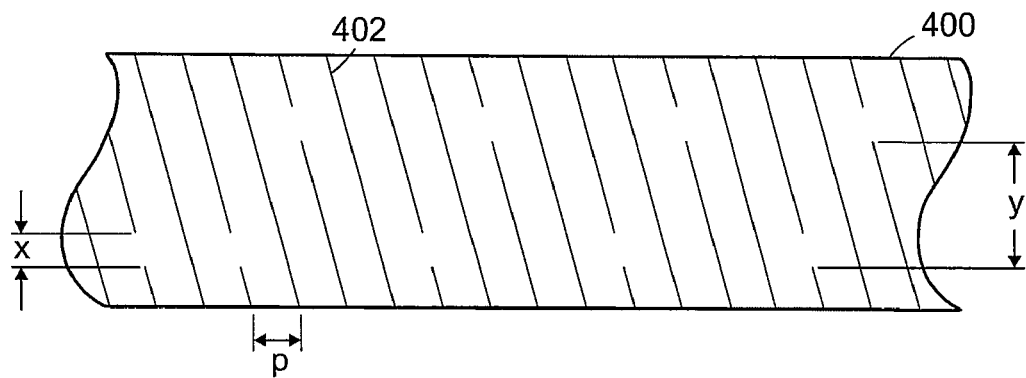
FIG. 16 is a side view of one embodiment of a steerable tube comprising an interrupted spiral cut pattern of slits.

FIG. 16 is a side view of one embodiment of a steerable overtube comprising an interrupted spiral cut pattern of slits. In one embodiment, the steerable segment 46 may comprise a steerable overtube 400 comprising slits 402 formed is an interrupted spiral cut pattern as shown in the embodiment illustrated in FIG. 16. The interrupted spiral cut pattern slits 402 may be defined by pitch "p," depth of interruption "x," and distance between interruptions "y." Each of these variables may be varied to achieve a desired bending radius, flexibility, and/or torquability of the steerable segment 400. In one embodiment, the interrupted spiral cut pattern slits 402 may be defined by a pitch "p" of about 1.5 mm, a depth of interruption "x" of about 16 mm, and a distance between interruptions "y" of about 1.5 mm. The interrupted spiral cut pattern slits 402 may be formed using a laser cutter. The width of the interrupted spiral cut pattern slits 402 is limited to the width of the cutting element, e.g., the laser spot site, which may be less than about 0.0254 mm.

Figure 17:
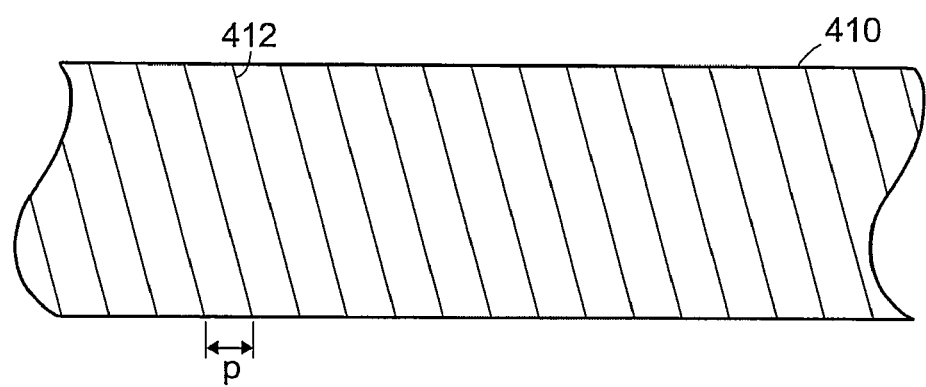
FIG. 17 is a side view of one embodiment of a steerable tube comprising a spiral cut pattern slits.

FIG. 17 is a side view of one embodiment of a steerable overtube comprising a spiral cut pattern of slits. In one embodiment, a steerable overtube 410 comprises slits 412 formed in a spiral cut pattern. The spiral cut pattern slits 412 may be defined by a pitch "p," which may be varied to achieve a desired bending radius, flexibility, and/or torquability of the steerable segment 410. In one embodiment, the spiral cut pattern slits 412 may be defined by a pitch "p" of about 1.5 mm. The spiral cut pattern slits 412 may be formed using a laser cutter or machine bit. The width of the spiral cut pattern slits 412 may be less than about 0.0254 mm, and is limited by width of the laser spot site.

Figure 18:
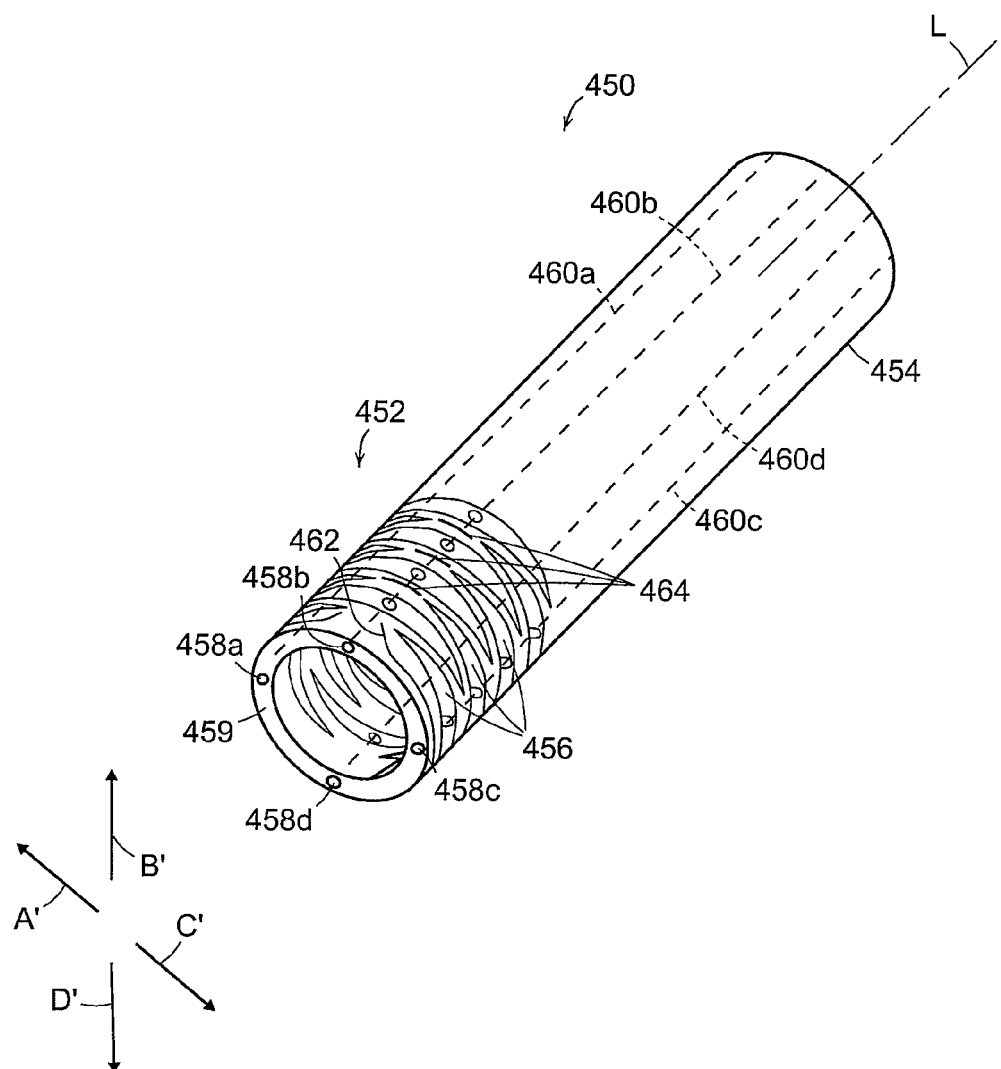
FIG. 18 illustrates one embodiment of a steerable segment comprising a multi-lumen steerable tube and a flexible segment.

FIG. 18 illustrates one embodiment of a steerable segment 450 comprising a steerable overtube 452 and a flexible segment 454. The flexible segment 454 may be substantially similar to the flexible overtube 12 previously described. The steerable overtube 456 comprises an elongate hollow body 459 defining a central opening suitable for receiving an endoscope therein. A plurality of apertures 456 and slits 462, 464 are formed on the body 459 of the steerable overtube 452 to make it flexible while still providing sufficient column strength. In one embodiment, the apertures 456 may be substantially similar to the apertures 142; the slits 462 may be substantially similar to the S-shaped slits 144; and the slits 464 may be substantially similar to the spiral slits 146; all of which are previously described with reference to FIGS. 11-13B. A plurality of embedded lumens 458a, 458b, 458c, and 458d are formed in the body 459 and extend along the longitudinally along axis "L." The lumen 458a-d also extend along the flexible segment 454. The embedded lumens 458a-d may have a diameter of about 1 mm. A plurality of pull cables 460a, 460b, 460c, 460d are disposed within the corresponding lumens 458a-d. The pull cables 460a-d are coupled to an actuation handle (not shown) at a proximal end. The actuation handle may be configured to apply tension to any one of or any combination of the pull cables 460a-d to articulate the steerable overtube 452 in any corresponding direction indicated by arrows A', B', C', and D'. The steerable overtube 452 may be articulated in other directions by applying tension to a combination of pull cables 460a-d.

As indicated above, the various devices disclosed herein can be used in a variety of surgical procedures, including endoscopic procedures, laparoscopic procedures, and in conventional open surgical procedures, including robotic-assisted surgery. In one exemplary endoscopic procedure, an elongate shaft of a surgical device, such as one previously disclosed herein, can be inserted through a natural orifice and a body lumen to position an end effector located at a distal end of the elongate shaft adjacent to tissue to be treated.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam. One skilled in the art will appreciate further features and advantages of the above-described embodiments. Accordingly, the embodiments are not to be limited by what has been particularly shown and described, except as indicated by the appended claims.

The invention claimed is:

1. An apparatus, comprising:
an elongate hollow metal body extending along a longitudinal axis, the hollow body defining a central opening and having a predetermined wall thickness,
a pattern of laser cut slits formed into the body, the slits defining a plurality of articulatable elements, wherein the plurality of articulatable elements enable active articulation of the body in a first plane and passive deflection in planes orthogonal to the first plane, wherein the pattern of slits comprises:
at least one aperture;
an S-shaped slit; and
a spiral slit; and
a plurality of rings disposed along an outer portion of the body along the longitudinal length, the plurality of rings are configured to receive a pull cable therethrough and a distal end of the pull cable is fixedly attached to a distal ring, wherein the pull cable is to articulate the body relative to the longitudinal axis when tension is applied to the pull cable.

2. The apparatus of claim 1, wherein the pattern of slits is positioned along the longitudinal axis in a predetermined arrangement.

3. The apparatus of claim 1, wherein the spiral slit is positioned between the aperture and the S-shaped slit.

4. The apparatus of claim 3, wherein an arrangement of the spiral slit positioned between the aperture and the S-shaped slit is repeated along the longitudinal axis of the body.

5. The apparatus of claim 1, wherein the at least one aperture is about 1 mm wide and each of the at least one apertures are spaced apart by about 4 mm.

6. The apparatus of claim 1, wherein the S-shaped slit begins on a first side of the body and wraps around to a second side of the body.

7. The apparatus of claim 6, wherein the S-shaped slit comprises:
a first portion that is perpendicular to the longitudinal axis;
a second portion that forms an angle $\theta$ with the longitudinal axis;
a third portion that is perpendicular to the longitudinal axis;
a fourth portion that forms an angle $\theta$ with the longitudinal axis; and
a fifth portion that is perpendicular to the longitudinal axis.

8. The apparatus of claim 7, wherein:
the first portion has a length of about 6 mm;
the second portion forms an angle $\theta$ between about 100 and about 110 degrees with the longitudinal axis and has a length of about 6 mm;
the third portion and has a length of about 10 mm;
the fourth portion has a length of about 6 mm; and
the fifth portion has a length of about 6 mm.

9. The apparatus of claim 1, wherein each revolution of the spiral slit is formed around one revolution of the body, wherein each revolution of the spiral slit has a predetermined overlap with a subsequent revolution of the spiral slit, and wherein each revolution of the spiral slit has a predetermined pitch.

10. The apparatus of claim 9, wherein the overlap is about 1.5 mm and the pitch is about 1.25 mm.

11. The apparatus of claim 1, wherein the spiral slit is formed as an interrupted spiral cut pattern defined by a pitch "p," a depth of interruption "x," and a distance between interruptions "y".

12. The apparatus of claim 11, wherein: the pitch "p" is about 1.5 mm; the depth of interruption "x" is about 16 mm; and the distance between interruptions "y" is about 1.5 mm.

13. The apparatus of claim 1, wherein the spiral slit is formed as a cut pattern defined by a pitch "p."

14. The apparatus of claim 13, wherein the pitch "p" is about 1.5 mm.

15. The apparatus of claim 1, wherein a portion of the slits are formed on an outer surface of the body without entirely penetrating the wall thickness.

16. The apparatus of claim 1, wherein the wall thickness of the body is in the range of about 0.25 mm to about 1 mm.

17. An apparatus, comprising:
a steerable tube;
a first layer of flexible material disposed on an inner portion of the steerable tube; and
a second layer of flexible material disposed on an outer portion of the steerable tube;
an elongate hollow metal body extending along a longitudinal axis, the hollow body defining a central opening and having a predetermined wall thickness;
a pattern of laser cut slits formed into the body, the slits defining a plurality of articulatable elements, wherein the plurality of articulatable elements enable active articulation of the body in a first plane and passive deflection in planes orthogonal to the first plane; and wherein the pattern of slits comprises:
- an aperture;
- an S-shaped slit; and
- a spiral slit; and a plurality of rings disposed along an outer portion of the body along the longitudinal length, the plurality of rings are configured to receive a pull cable therethrough and a distal end of the pull cable is fixedly attached to a distal ring, wherein the pull cable is to articulate the body relative to the longitudinal axis when tension is applied to the pull cable.

18. The apparatus of claim 17, wherein the pattern of slits is positioned along the longitudinal axis in a predetermined arrangement.

19. The apparatus of claim 17, wherein the spiral slit is positioned between the aperture and the S-shaped slit.

20. The apparatus of claim 19, wherein an arrangement of the spiral slit positioned between the aperture and the S-shaped slit is repeated along the longitudinal axis of the body.

21. The apparatus of claim 17, wherein the S-shaped slit begins on a first side of the body and wraps around to a second side of the body.

22. The apparatus of claim 21, wherein the S-shaped slit comprises:
- a first portion that is perpendicular to the longitudinal axis;
- a second portion that forms an angle θ with the longitudinal axis;
- a third portion that is perpendicular to the longitudinal axis;
- a fourth portion that forms an angle θ with the longitudinal axis; and
- a fifth portion that is perpendicular to the longitudinal axis.

23. The steerable apparatus of claim 17, wherein the spiral slit makes one revolution around the body with a predetermined overlap and pitch.

24. The steerable apparatus of claim 17, wherein the spiral slit is formed as an interrupted spiral cut pattern defined by a pitch "p," a depth of interruption "x," and a distance between interruptions "y."

25. The steerable apparatus of claim 17, wherein the spiral slit is formed as a cut pattern defined by a pitch "p."

26. The apparatus of claim 17, wherein a portion of the slits are formed on an outer surface of the body without entirely penetrating the wall thickness.

27. The apparatus of claim 17, wherein the wall thickness of the body is in the range of about 0.25 mm to about 1 mm.

28. An apparatus, comprising:

an elongate hollow metal body extending along a longitudinal axis, the hollow body defining a central opening and having a predetermined wall thickness;

a pattern of laser cut slits formed into the body, the slits defining a plurality of articulatable elements, wherein the plurality of articulatable elements enable active articulation of the body in a first plane and passive deflection in planes orthogonal to the first plane;

wherein the pattern of slits comprises:
- an aperture;
- an S-shaped slit; and
- a spiral slit; and at least one embedded lumen formed in the body extending along the longitudinal axis, the embedded lumen is configured to receive a pull cable therethrough; and a plurality of rings disposed along an outer portion of the body along the longitudinal length, the plurality of rings are configured to receive the pull cable therethrough and a distal end of the pull cable is fixedly attached to a distal ring, wherein the pull cable is to articulate the body relative to the longitudinal axis when tension is applied to the pull cable.

29. The apparatus of claim 28, comprising:

a plurality of embedded lumen formed in the body extending along the longitudinal axis, the plurality of embedded lumen is configured to receive a plurality of pull cables therethrough.

* * * * *